(12) United States Patent
Yoshioka et al.

(10) Patent No.: US 8,952,125 B2
(45) Date of Patent: Feb. 10, 2015

(54) POLYOXYETHYLENE DERIVATIVE HAVING PLURAL HYDROXYL GROUPS AT TERMINAL END THEREOF

(75) Inventors: Hiroki Yoshioka, Kanagawa (JP); Takashi Matani, Kanagawa (JP); Yuji Yamamoto, Kanagawa (JP)

(73) Assignee: NOF Corporation, Tokyo (JP)

( * ) Notice: Subject to any disclaimer, the term of this patent is extended or adjusted under 35 U.S.C. 154(b) by 236 days.

(21) Appl. No.: 13/435,556

(22) Filed: Mar. 30, 2012

(65) Prior Publication Data
US 2012/0322955 A1 Dec. 20, 2012

(30) Foreign Application Priority Data
Mar. 30, 2011 (JP) ................................ 2011-076682

(51) Int. Cl.
| C08G 65/04 | (2006.01) |
| C08G 65/34 | (2006.01) |
| A61K 47/48 | (2006.01) |
| C08G 65/26 | (2006.01) |
| C08G 65/333 | (2006.01) |
| C08G 65/00 | (2006.01) |

(52) U.S. Cl.
CPC ...... *A61K 47/48215* (2013.01); *C08G 65/2606* (2013.01); *C08G 65/33337* (2013.01); *C08L 2203/02* (2013.01)
USPC .......................................... 528/421; 528/425

(58) Field of Classification Search
USPC ................................................ 528/421, 425
See application file for complete search history.

(56) References Cited

U.S. PATENT DOCUMENTS

| 2004/0062748 A1 | 4/2004 | Martinez et al. |
| 2008/0019918 A1 | 1/2008 | Aoki et al. |
| 2010/0029899 A1 | 2/2010 | Sakanoue et al. |
| 2010/0261863 A1 | 10/2010 | Takehana et al. |
| 2010/0286361 A1 | 11/2010 | Yoshimura et al. |

FOREIGN PATENT DOCUMENTS

| JP | 2006-510601 A | 3/2006 |
| JP | 2007-31554 A | 2/2007 |
| JP | 2008-188557 A | 8/2008 |
| JP | 2010-235450 A | 10/2010 |
| JP | 2010-254978 A | 11/2010 |
| WO | 2005/037911 A2 | 4/2005 |
| WO | 2006/028129 A1 | 3/2006 |
| WO | 2008/096904 A1 | 8/2008 |
| WO | 2008/105514 A1 | 9/2008 |
| WO | 2010/114074 A1 | 10/2010 |

OTHER PUBLICATIONS

Tatsuhiro Ishida et al., "PEGylated liposomes elicit an anti-PEG IgM response in a T cell-independent manner"; Journal of Controlled Release; vol. 122; 2007; pp. 349-355.
Wim Jiskoot, et al.; "Immunological Risk of Injectable Drug Delivery Systems"; Pharmaceutical Research; vol. 26; No. 6; Jun. 2009; pp. 1303-1314.
International Search Report (PCT/ISA/210), dated May 22, 2012, issued by the International Searching Authority in counterpart International Application No. PCT/JP2012/058069.

*Primary Examiner* — Duc Truong
(74) *Attorney, Agent, or Firm* — Sughrue Mion, PLLC

(57) ABSTRACT

A polyoxyethylene derivative represented by the formula (1):

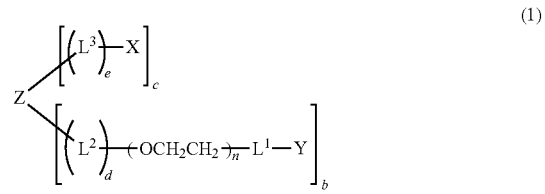

wherein a whole molecular weight of the polyoxyethylene derivative is 500 to 160,000; n is 5 to 3650; $L^1$, $L^2$, and $L^3$ each independently represent an alkylene group, a phenylene group, an ester bond, an amide bond, an ether bond, a urethane bond, a carbonate bond, a secondary amino group, or a combination thereof; X represents a functional group capable of reacting with a bio-related substance; Y represents a hydrophilic group having plural hydroxyl groups made from a residual group of xylitol or volemitol or a residual group of polyglycerin of trimer to 31-mer; Z represents a residual group of a compound having 2 to 5 active hydrogen atoms; b and c are as follows: $1 \leq b \leq 4$, $1 \leq c \leq 4$, and $2 \leq b+c \leq 5$; and d and e each independently are 0 or 1.

6 Claims, No Drawings

POLYOXYETHYLENE DERIVATIVE HAVING PLURAL HYDROXYL GROUPS AT TERMINAL END THEREOF

FIELD OF THE INVENTION

The present invention relates to a polyoxyethylene derivative having plural hydroxyl groups at a terminal end thereof, which is used in uses for modifying bio-related substances.

BACKGROUND OF THE INVENTION

Recently, development on medicaments have been carried out, which use bio-related substances such as intercellular signaling substances such as hormones and cytokines, antibodies, and enzymes. When injected to a living body, these bio-related substances are usually cleared from the body because of the filtration through glomeruli in the kidney and the uptake by macrophages in the liver, spleen, and the like. Therefore, they have short half-lives in blood and hence it is difficult to obtain a sufficient pharmacological effect. For solving the problems, it is attempted to encapsulate the bio-related substances in liposomes or polymer micelles and to chemically modify the bio-related substances with an amphiphatic polymer such as a sugar chain or polyethylene glycol or albumin. By these attempts, the behavior of the bio-related substances in a living body is improved through increase in their molecular weight or formation of a hydration layer. Moreover, it is also known that effects of decreasing toxicity and antigenicity and enhancing solubility of sparingly water-soluble pharmaceuticals are obtained by the modification with polyoxyethylene.

Non-Patent Documents 1 and 2 have report that there is a case of an ABC (accelerated blood clearance) phenomenon in which half-lives in blood decrease at the second or later administration as compared with the case at the first administration when liposomes or nano particles modified with polyoxyethylene are repeatedly administered to the same individual. It is considered that this is because an antibody to the polyoxyethylene with which the liposomes or nano particles have been modified is expressed and it is said that the antibody recognizes various sites, such as a terminal end of the polyoxyethylene chain and a repeating structure of the polyoxyethylene. On the other hand, there is a reported example that liposomes and nano particles modified with some hydrophilic polymers such as polyglycerin hardly induce the ABC phenomenon. However, with hydrophilic polymers other than the polyoxyethylene, a sufficient circulation in blood cannot be obtained and also the polymers are poor in examples in clinical use, so that they are not sufficient as alternatives of polyoxyethylene.

On the other hand, in Patent Document 1, there is a description relating to a bio-related substance modified with a polyoxyethylene derivative having one hydroxyl group at a terminal end thereof. When a polyoxyethylene derivative having a hydroxyl group at a terminal end thereof is used, data showing decreased antigenicity are obtained as compared with the case of a polyoxyethylene derivative having a alkoxy group at a terminal end thereof. Such placement of the hydroxyl group at the terminal end of the polyoxyethylene derivative is considered to be one remedial measure for contributing a decrease in antigenicity of polyoxyethylene. However, since the polyoxyethylene derivative described in the document is purified using a reverse-phase chromatography, the yield decreases to a large extent and hence the derivative is not suitable for industrial production. Moreover, in recent years, development of pharmaceutical agents showing more improved circulation in blood has been in progress and there is a need for further decreasing antigenicity.

Since the placement of plural hydroxyl groups at a terminal end of polyoxyethylene leads to formation of a stronger and larger hydrated layer around a carrier, it is considered that the interaction with an opsonin is lowered and, as a result, the antigenicity can be further decreased. There are the following documents on polyoxyethylene having plural hydroxyl groups.

In many documents including Patent Documents 2 and 3, there are descriptions relating to targeting-type preparations wherein a monosaccharide or polysaccharide having plural hydroxyl groups is introduced into a terminal end of a hydrophilic polymer and a drug is bonded thereto. However, the saccharides are used for getting a targeting property through a carbohydrate recognition mechanism present in a living body and it is not intended to improve antigenicity.

Patent Documents 4 and 5 describes hydrophobic polyoxyalkylene having a polyglycerin derivative with a large number of hydroxyl groups. Such hydrophobic polyoxyalkylene is a surfactant which utilizes the hydrophilicity of polyglycerin. In these documents, only examples of hydrophobic polyoxyalkylene are shown and it is difficult to obtain a highly pure polyoxyethylene derivative suitable for modifying bio-related substances by the production methods described therein.

Patent Document 6 describes a copolymer of polyoxyethylene and polyglycidol. In the method of manufacturing a random or block polymer described in the document, the polyglycidol is converted into branched polymers having plural branches and into a mixture of polymers having various structures. As a raw material for medicaments, a highly pure compound having a single structure is required and a mixture is not preferred. Furthermore, it is necessary for a mixture to define a compositional ratio and the like of components contained therein at application for registration of pharmaceutical raw materials and thus much difficulty exists. Moreover, it is difficult to control the number of hydroxyl groups in the polymer at the polymerization of glycidol and hence there is a problem that viscosity of a polymer solution increases when the number of hydroxyl groups increases.

As above, it is a current situation that a polyoxyethylene derivative suitable for modification of bio-related substances, having plural hydroxyl groups that can improve half-lives in blood and antigenicity at one terminal end, and capable of industrial production has not been obtained.

PRIOR ART DOCUMENTS

Patent Documents

Patent Document 1: JP-T-2006-510601
Patent Document 2: WO2006/028129
Patent Document 3: WO2008/096904
Patent Document 4: JP-A-2007-31554
Patent Document 5: JP-A-2008-188557
Patent Document 6: WO2005/037911

Non-Patent Documents

Non-Patent Document 1: T. Ishida, H. Kiwada, et al., J. control. Release. 122, 349-355 (2007)
Non-Patent Document 2: W. Jiskoot, R. M. F. van Schie, et al., Pharmaceutical Research, 26, 6, 1303-1314 (2009)

SUMMARY OF THE INVENTION

An object of the invention is to provide a novel polyoxyethylene derivative having plural hydroxyl groups at a terminal end thereof. More specifically, it is to provide a polyoxyethylene derivative having plural hydroxyl groups at a terminal end thereof, which can be effectively used in uses for modifying bio-related substances and can be industrially produced.

As a result of the extensive studies for solving the above problems, the present inventors have accomplished a polyoxyethylene derivative having plural hydroxyl groups at a terminal end thereof, the derivative comprising the following constitution.

Namely, the invention is as follows.

[1] A polyoxyethylene derivative represented by the formula (1):

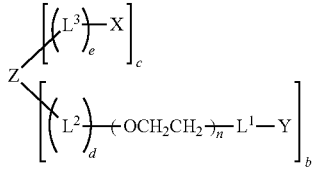

(1)

wherein a whole molecular weight of the polyoxyethylene derivative is 500 to 160,000; n is 5 to 3650; $L^1$, $L^2$, and $L^3$ each independently represent an alkylene group, a phenylene group, an ester bond, an amide bond, an ether bond, a urethane bond, a carbonate bond, a secondary amino group, or a combination thereof; X represents a functional group capable of reacting with a bio-related substance; Y represents a hydrophilic group having plural hydroxyl groups made from a residual group of xylitol or volemitol or a residual group of polyglycerin of trimer to 31-mer; Z represents a residual group of a compound having 2 to 5 active hydrogen atoms; b and c are as follows: and $1 \leq b \leq 4$, $1 \leq c \leq 4$, $2 \leq b \leq 5$; and d and e each independently are 0 or 1.

[2] A polyoxyethylene derivative represented by the formula (2):

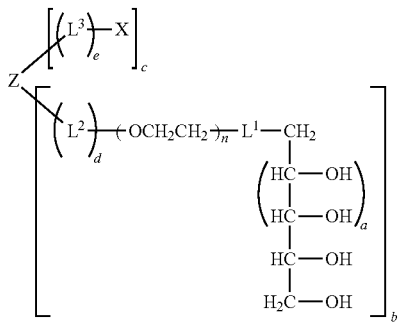

(2)

wherein a whole molecular weight of the polyoxyethylene derivative is 500 to 160,000; n is 5 to 3650; $L^1$, $L^2$, and $L^3$ each independently represent an alkylene group, a phenylene group, an ester bond, an amide bond, an ether bond, a urethane bond, a carbonate bond, a secondary amino group, or a combination thereof; X represents a functional group capable of reacting with a bio-related substance; Z represents a residual group of a compound having 2 to 5 active hydrogen atoms; a is 1 or 2; b and c are as follows: $1 \leq b \leq 4$, $1 \leq c \leq 4$, and $2 \leq b+c \leq 5$; and d and e are 0 or 1.

[3] The polyoxyethylene derivative according to the above [2], which is a polyoxyethylene derivative represented by the following formula (3), wherein Z is an ethylene glycol residual group, b is 1, c is 1, d is 0, and e is 1 in the formula (2):

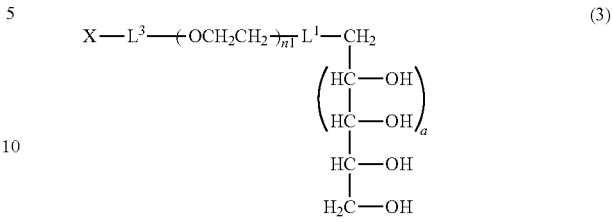

(3)

wherein $L^1$ and $L^3$ each independently represent an alkylene group, a phenylene group, an ester bond, an amide bond, an ether bond, a urethane bond, a carbonate bond, a secondary amino group, or a combination thereof; X represents a functional group capable of reacting with a bio-related substance; a is 1 or 2; and n1 is 11 to 3650.

[4] The polyoxyethylene derivative according to the above [2], which is a polyoxyethylene derivative represented by the following formula (4), wherein Z is a glycerin residual group, b is 2, c is 1, and d is 0 in the formula (2):

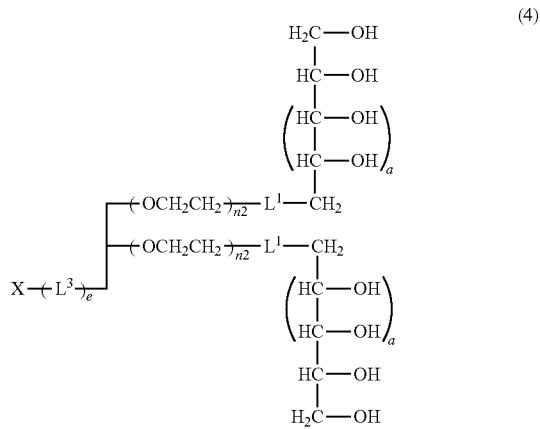

(4)

wherein $L^1$ and $L^3$ each independently represent an alkylene group, a phenylene group, an ester bond, an amide bond, an ether bond, a urethane bond, a carbonate bond, a secondary amino group, or a combination thereof; X represents a functional group capable of reacting with a bio-related substance; a is 1 or 2; e is 0 or 1; and n2 is 11 to 1825.

[5] The polyoxyethylene derivative according to the above [1], wherein, in the formula (1), X is an active ester group, an active carbonate group, an aldehyde group, an isocyanate group, an isothiocyanate group, an epoxy group, a carboxyl group, a thiol group, a maleimido group, a substituted maleimido group, a hydrazido group, a dithiopyridine group, a substituted sulfonate group, a vinylsulfone group, an amino group, an oxyamino group, an iodoacetamido group, an alkylcarbonyl group, an alkenyl group, an alkynyl group, or an azido group.

[6] The polyoxyethylene derivative according to the above [2], wherein, in the formula (2), X is an active ester group, an active carbonate group, an aldehyde group, an isocyanate group, an isothiocyanate group, an epoxy group, a carboxyl group, a thiol group, a maleimido group, a substituted maleimido group, a hydrazido group, a dithiopyridine group, a substituted sulfonate group, a vinylsulfone group, an amino group, an oxyamino group, an iodoacetamido group, an alkylcarbonyl group, an alkenyl group, an alkynyl group, or an azido group.

[7] The polyoxyethylene derivative according to the above [3], wherein, in the formula (3), X is an active ester group, an active carbonate group, an aldehyde group, an isocyanate group, an isothiocyanate group, an epoxy group, a carboxyl group, a thiol group, a maleimido group, a substituted maleimido group, a hydrazido group, a dithiopyridine group, a substituted sulfonate group, a vinylsulfone group, an amino group, an oxyamino group, an iodoacetamido group, an alkylcarbonyl group, an alkenyl group, an alkynyl group, or an azido group.

[8] The polyoxyethylene derivative according to the above [4], wherein, in the formula (4), X is an active ester group, an active carbonate group, an aldehyde group, an isocyanate group, an isothiocyanate group, an epoxy group, a carboxyl group, a thiol group, a maleimido group, a substituted maleimido group, a hydrazido group, a dithiopyridine group, a substituted sulfonate group, a vinylsulfone group, an amino group, an oxyamino group, an iodoacetamido group, an alkylcarbonyl group, an alkenyl group, an alkynyl group, or an azido group.

In the chemical formulae in the present Description, a portion:

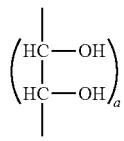

defines a 1,2-dihydroxyethylene group as a repeating unit, and has the same meaning as the following:

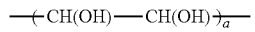

Since the polyoxyethylene derivative of the invention has plural hydroxyl groups (preferably 4 or more hydroxyl groups) at a terminal end thereof, in the case of modifying a bio-related substance, a large hydrated layer induced by strong hydrogen bonds is formed around the bio-related substance. Therefore, the modified bio-related substance has a decreased interaction with an opsonin or a cell surface composing each tissue in a body to reduce transitional ability to each tissue, whereby half-lives in blood are improved. Moreover, since a hydrophilic molecule having plural hydroxyl groups derived from a sugar alcohol such as xylitol or volemitol or polyglycerin of trimer to 31-mer is bonded to a terminal end of the polyoxyethylene, expression of an antibody recognizing an alkoxy group at a terminal end of the polyoxyethylene chain in this type of conventional polyoxyethylene derivative can be effectively suppressed. Furthermore, since such a hydrophilic molecule exhibits strong hydration ability at the terminal end of the polyoxyethylene chain, the derivative can be stably used even under high salt concentration conditions. Also, since the polyoxyethylene derivative of the invention can be efficiently manufactured in high purity, it can be industrially manufactured.

DETAILED DESCRIPTION OF THE INVENTION

The polyoxyethylene derivative according to the invention is a polyoxyethylene derivative represented by the formula (1) (hereinafter also referred to as "polyoxyethylene derivative (1) of the invention"):

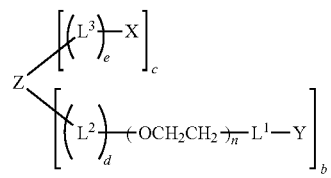

wherein a whole molecular weight of the polyoxyethylene derivative is 500 to 160,000; n is 5 to 3650; $L^1$, $L^2$, and $L^3$ each independently represent an alkylene group, a phenylene group, an ester bond, an amide bond, an ether bond, a urethane bond, a carbonate bond, a secondary amino group, or a combination thereof; X represents a functional group capable of reacting with a bio-related substance; Y represents a hydrophilic group having plural hydroxyl groups made from a residual group of xylitol or volemitol or a residual group of polyglycerin of trimer to 31-mer; Z represents a residual group of a compound having 2 to 5 active hydrogen atoms; b and c are as follows: $1 \leq b \leq 4$, $1 \leq c \leq 4$, and $2 \leq b+c \leq 5$; and d and e each independently are 0 or 1.

The molecular weight of the polyoxyethylene derivative of the formula (1) is usually 500 to 160,000, preferably 1,000 to 80,000, and further preferably 2,000 to 40,000.

$L^1$, $L^2$, and $L^3$ in the formula (1) represent a linker connecting the hydrophilic group Y having plural hydroxyl groups and the polyoxyethylene with a covalent bond, a linker connecting the polyoxyethylene and the residual group Z of the compound having 2 to 5 active hydrogen atoms with a covalent bond, and a linker connecting the residual group Z of the compound having 2 to 5 active hydrogen atoms and the functional group X capable of reacting with a bio-related substance, respectively.

These linkers are not particularly limited as far as they are groups capable of forming a covalent bond. The linker is preferably an alkylene group, a phenylene group, an ester bond, an amide bond, an ether bond, a urethane bond, a carbonate bond, a secondary amino group, or a combination thereof, more preferably an alkylene group, a phenylene group, or a combination of an ester bond, an amide bond, an ether bond, a urethane bond, a carbonate bond, or a secondary amino group with one or two alkylene groups, and particularly preferable embodiments are those shown in the following group (I).

Group (I):

wherein s is an integer of 0 or 1 to 10.

In the formulae (formula (z1) to formula (z6)), s in the formula represents an integer of 1 to 10, preferably an integer of 1 to 6, and further preferably an integer of 1 to 3. Moreover, in the formula (z3) and the formula (z6), two s groups in the formulae may be the same or different but is preferably the same.

Particularly preferable embodiments of $L^1$ are —OCO—NH—, —O—, and —($CH_2$)s-CO—NH—.

The "functional group capable of reacting with a bio-related substance" represented by X in the formula (1) is not particularly limited as far as it is a functional group capable of chemically bonding to a functional group such as an amino group, a mercapto group, an aldehyde group, a carboxyl group, an unsaturated bond, or an azido group that a bio-related substance has. Specifically, there may be mentioned an active ester group, an active carbonate group, an aldehyde group, an isocyanate group, an isothiocyanate group, an epoxy group, a carboxyl group, a thiol group, a maleimido group, a substituted maleimido group, a hydrazido group, a dithiopyridine group, a substituted sulfonate group, a vinylsulfone group, an amino group, an oxyamino group, an iodoacetamido group, an alkylcarbonyl group, an alkenyl group, an alkynyl group, or an azido group.

In suitable embodiments, such a functional group X can be classified into the following group (II), group (III), group (IV), group (V), group (VI), and group (VII).

Group (II): functional groups capable of reacting with an amino group that a bio-related substance has The following (a), (b), (c), (d), (e), (f), (i)

Group (III): functional groups capable of reacting with a mercapto group that a bio-related substance has The following (a), (b), (c), (d), (e), (f), (g), (h), (i), (j)

Group (IV): functional groups capable of reacting with an aldehyde group that a bio-related substance has The following (g), (k), (l), (m)

Group (V): functional groups capable of reacting with a carboxyl group that a bio-related substance has The following (g), (k), (l), (m)

Group (VI): functional groups capable of reacting with an unsaturated bond that a bio-related substance has The following (g), (k), (n)

Group (VII): functional groups capable of reacting with an azido group that a bio-related substance has The following (j)

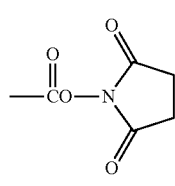

(a)

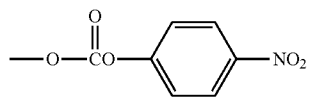

(b)

(c)

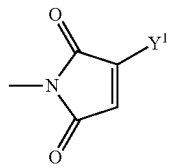

(d)

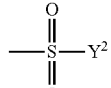

(e)

—COOH (f)

—SH (g)

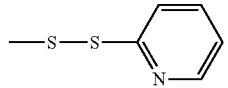

(h)

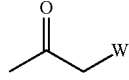

(i)

—C≡C—$Y^3$ (j)

—$NH_2$ (k)

—O—$NH_2$ (l)

—$NHNH_2$ (m)

—$N_3$ (n)

In the functional group (i), W in the formula represents a halogen atom such as a chlorine atom (Cl), a bromine atom (Br), or an iodine atom (I), preferably Br or I, and more preferably I.

Moreover, in the functional group (d) and the functional group (j), $Y^1$ and $Y^3$ in the formulae each independently represent a hydrogen atom or a hydrocarbon group having 1 to 5 carbon atoms and preferably a hydrocarbon group having 1 to 5 carbon atoms. The hydrocarbon group having 1 to 5 carbon atoms specifically includes a methyl group, an ethyl group, a propyl group, an isopropyl group, a butyl group, a tertiary butyl group, and the like. Preferred are a methyl group and an ethyl group.

Furthermore, in the functional group (e), $Y^2$ in the formula is a hydrocarbon group having 1 to 10 carbon atoms which may contain a fluorine atom. Specifically, $Y^2$ includes a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy)phenyl group, and the like. Preferred are a methyl group, a vinyl group, a 4-methylphenyl group, and a 2,2,2-trifluoroethyl group.

The active ester group is an ester group in which the carboxyl group is condensed with an alkoxy group having high elimination ability. There may be mentioned esters of the carboxyl group with nitrophenol, N-hydroxysuccinimide, pentafluorophenol, and the like, and preferred is an ester group in which the carboxyl group is condensed with N-hydroxysuccinimide.

The active carbonate group is a carbonate group having an alkoxy group having high elimination ability. The alkoxy group having high elimination ability includes nitrophenol, N-hydroxysuccinimide, pentafluorophenol, and the like, and preferred is a carbonate group which is bonded to nitrophenol or N-hydroxysuccinimide.

The substituted maleimido group is a maleimido group in which a hydrocarbon group is bonded to one carbon atom of the double bond of the maleimido group. The hydrocarbon group specifically includes a methyl group, an ethyl group, a propyl group, an isopropyl group, a butyl group, a tertiary butyl group, and the like. Preferred are a methyl group and an ethyl group.

The substituted sulfonate group is a sulfonate group in which a hydrocarbon group which may contain a fluorine atom is bonded to the sulfur atom of the sulfonate group. The hydrocarbon group which may contain a fluorine atom specifically includes a methyl group, an ethyl group, a propyl group, an isopropyl group, a butyl group, a tertiary butyl group, a hexyl group, a nonyl group, a vinyl group, a phenyl group, a benzyl group, a 4-methylphenyl group, a trifluoromethyl group, a 2,2,2-trifluoroethyl group, a 4-(trifluoromethoxy)phenyl group, and the like. Preferred are a methyl group, a vinyl group, a 4-methylphenyl group, and a 2,2,2-trifluoroethyl group.

The "residual group of a compound having 2 to 5 active hydrogen atoms" represented by Z in the formula (1) includes a residual group to be obtained by removing a hydroxyl group from a polyhydric alcohol having 2 to 5 hydroxyl groups (ethylene glycol, glycerin, diglycerin, pentaerythritol, xylitol, and the like), a residual group to be obtained by removing one active hydrogen atom from lysine, a residual group to be obtained by removing OH of the carboxyl group from aspartic acid, a residual group to be obtained by removing OH of the carboxyl group from glutamic acid, and the like. Preferred are residual groups of ethylene glycol, glycerin, pentaerythritol, xylitol, and lysine and further preferred are residual groups of ethylene glycol and glycerin.

b in the formula (1) represents the number of polyoxyethylene chains to which the hydrophilic group Y having plural hydroxyl groups are bonded and c represents the number of functional groups X capable of reacting with a bio-related substance. b and c are as follows: $1 \leq b \leq 4$, $1 \leq c \leq 4$, and $2 \leq b+c \leq 5$, preferably $1 \leq b \leq 2$, $1 \leq c \leq 2$, and $2 \leq b+c \leq 4$.

Moreover, in the formula (1), d and e represent presence or absence of the linkers. The linker is absent in the case where d is 0 and the linker is present in the case where d is 1.

Y in the formula (1) represents a hydrophilic group having plural groups made from a residual group of xylitol or volemitol or a residual group of polyglycerin of trimer to 31-mer. Here, the "residual group of xylitol or volemitol or residual group of polyglycerin of trimer to 31-mer" means a residual group to be obtained by removing the hydroxyl group that has contributed to the bonding reaction to the polyoxyethylene chain, in xylitol or volemitol or polyglycerin of trimer to 31-mer.

In the case where the hydrophilic group Y in the formula (1) is a residual group of xylitol or volemitol, any of the hydroxyl groups in 1-position and 3-position of xylitol or volemitol may be bonded to the polyoxyethylene chain but preferably, the hydroxyl group in the 1-position is bonded thereto. Moreover, in the case where the hydrophilic group Y in the formula (1) is polyglycerin, the polyglycerin may be liner one or a dendrimer but is preferably a dendrimer. Moreover, it is preferably trimer, heptamer, pentadecamer, or 31-mer and more preferably trimer or heptamer.

The following formula (2) represents a polyoxyethylene derivative of a preferable embodiment, in which the hydrophilic group Y having plural hydroxyl groups is made from a residual group of xylitol or volemitol. The case where a in the formula is 1 is a xylitol structure and the case where a is 2 is a volmitol structure.

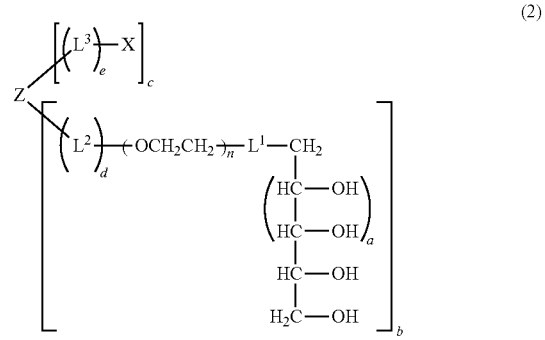

(2)

wherein a whole molecular weight of the polyoxyethylene derivative is 500 to 160,000; n is 5 to 3650; $L^1$, $L^2$, $L^3$, X, Z, a, b, c, d, and e have the same meanings as mentioned above.

Moreover, in the polyoxyethylene derivative of the formula (2), a case that Z is an ethylene glycol residual group, b is 1, c is 1, d is 0, and e is 1 is more preferred, and the following formula (3) represents a polyoxyethylene derivative of such a preferable embodiment.

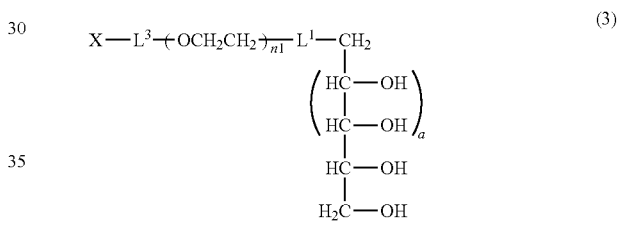

(3)

wherein $L^1$, $L^3$, X, and a have the same meanings as mentioned above and n1 is 11 to 3650.

n1 in the formula (3) is the number of average addition moles of the oxyethylene group and n1 is usually 11 to 3650, preferably 22 to 1825, and further preferably 44 to 910.

Moreover, in the polyoxyethylene derivative of the formula (2), a case that Z is a glycerin residual group, b is 2, c is 1, and d is 0 is more preferred, and the following formula (4) represents a polyoxyethylene derivative of such a preferable embodiment.

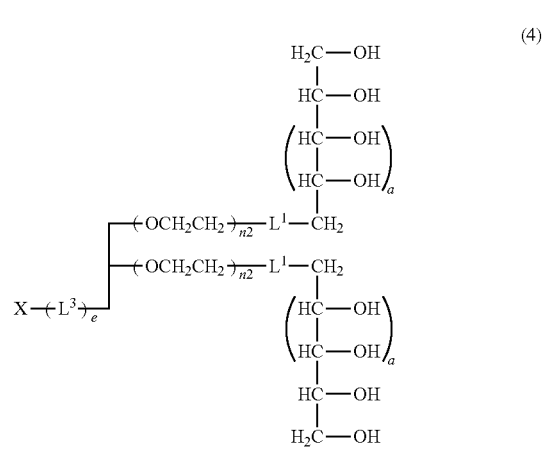

(4)

wherein $L^1$, $L^3$, X, a, and e have the same meanings as mentioned above and n2 is 11 to 1825.

n2 in the formula (4) is the number of average addition moles of the oxyethylene group and n2 is usually 11 to 1825, preferably 22 to 1370, and further preferably 44 to 925.

The polyoxyethylene derivative of the invention can be, for example, manufactured through a route shown in the following process drawing (process drawing (I)).

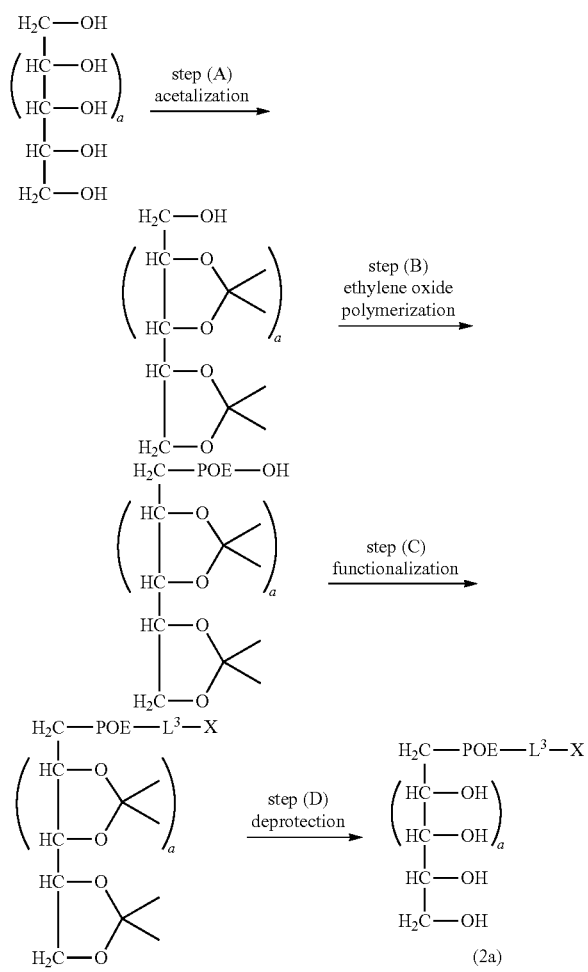

(2a)

wherein POE represents a polyoxyethylene chain and $L^3$, X, and a have the same meanings as mentioned above.

The step (A) is a step of protecting even-numbered hydroxyl groups of the polyhydric alcohol by cyclic acetalization.

The step (B) is a step of polymerizing ethylene oxide to the remaining hydroxyl group of the polyhydric alcohol protected in the step (A) in an amount of 11 to 3650 moles.

The step (C) is a step of functionalizing the hydroxyl group at a terminal end of the polyoxyethylene derivative. Depending on the kind of the functional group, it is also possible to further perform functionalization after deacetalization of the step (D). Depending on the kind of the functional group, it is possible to perform deacetalization of the step (D) simultaneously with the functionalization.

The step (D) is a step of cleaving the cyclic acetal structure. Four hydroxyl groups are produced in the case of a=1 and six hydroxyl groups are produced in the case of a=2.

By performing the above steps (A), (B), (C), and (D), the polyoxyethylene derivative represented by the formula (2a) (polyoxyethylene derivative (2a)) is manufactured.

The following will further describe preferable specific examples of the method for manufacturing the polyoxyethylene derivative (2a). Since the derivative can be manufactured by the same manufacturing method in both cases of a=1 and a=2, the derivative of a=1, i.e., the polyoxyethylene derivative represented by the following formula (10) (polyoxyethylene derivative (10)) will be described.

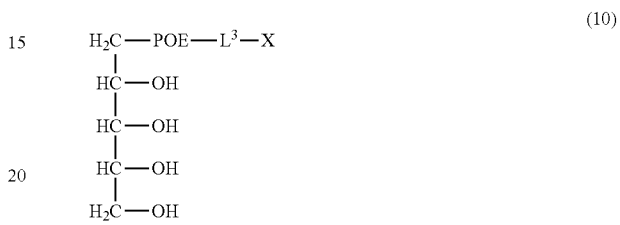

wherein POE, $L^3$, and X have the same meanings as mentioned above.

The polyoxyethylene derivative (10) can be manufactured by the route shown in the following process drawing (process drawing II).

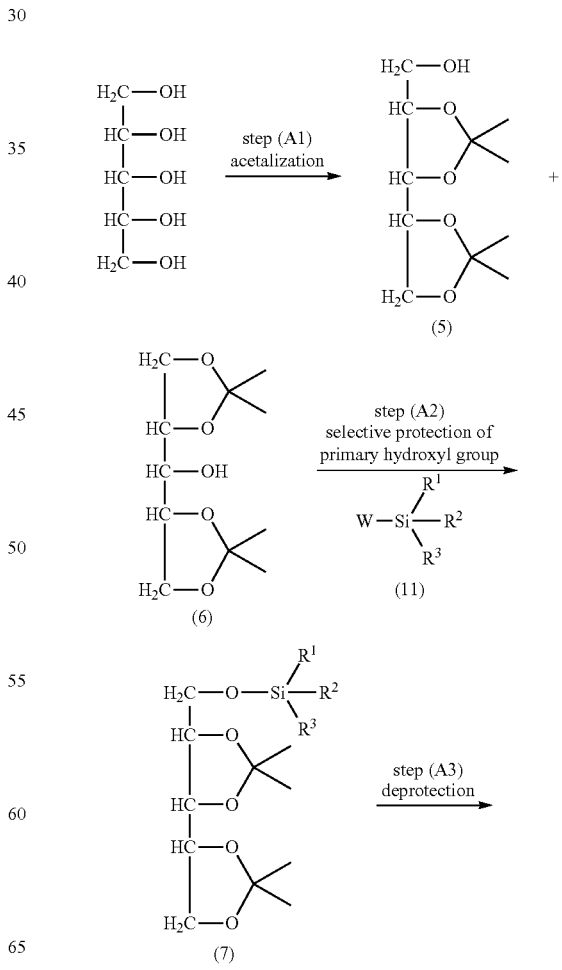

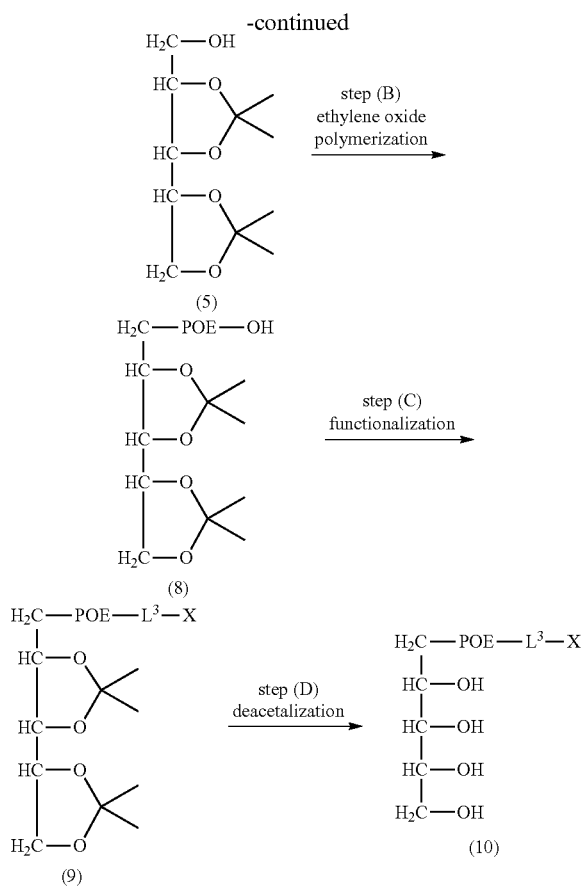

wherein $R^1$, $R^2$, and $R^3$ each independently represent a hydrocarbon group having 1 to 10 carbon atoms; W represents a halogen atom; and POE, $L^3$, and X have the same meanings as mentioned above.

The step (A) comprises three steps of the following (A1), (A2), and (A3).

The step (A1) is a step of cyclic acetalization of the hydroxyl groups of a polyhydric alcohol. In the step, four hydroxyl groups of xylitol is subjected to cyclic acetalization to obtain a mixture of 1,2,3,4-diisopropylidenexylitol represented by the formula (5) and 1,2,4,5-diisopropylidenexylitol isomer represented by the formula (6).

A method for acetalization is not particularly limited as far as it is a common protection method of a hydroxyl group as described in PROTECTIVE GROUPS IN ORGANIC SYNTHESIS (THEODORA W. GREENE et al) and the like. Specifically, the mixture of the compounds represented by the formulae (5) and (6) is obtained in a molar ratio of about 9:1 by reacting xylitol with 2,2-dimethoxypropane in the presence of an acid catalyst such as acetic acid, hydrochloric acid, phosphoric acid, p-toluenesulfonic acid, or p-toluenesulfonic acid monohydrate.

The amount of the acid to be used is preferably $5 \times 10^{-6}$ to $5 \times 10^{-3}$ equivalent and more preferably $5 \times 10^{-5}$ to $5 \times 10^{-4}$ equivalent to xylitol.

The amount of 2,2-dimethoxypropane to be used is preferably 2.0 to 4.0 equivalents and more preferably 2.5 to 3.5 equivalents to xylitol.

The reaction can be carried out in a solvent or without any solvent. In the case where a solvent is used, for example, dimethylformamide, dichloromethane, or the like can be used but no solvent is preferred.

The reaction temperature is usually 0 to 90° C. and preferably 30 to 80° C. The reaction time is preferably 1 to 24 hours. When the reaction time is short, the reaction proceeds insufficiently.

Unacetalized impurities produced as by-products in the reaction, impurities in which xylitol molecules are bonded to each other with acetal, or the like are preferably removed by purification. The purification is not particularly limited and column chromatography, extraction, distillation, and/or supercritical extraction can be performed. Preferably, the purification can be performed by distillation under normal pressure.

The step (A2) is a step of selectively protecting only one of the structural isomers and separating it from another isomer. Only the primary hydroxyl group of 1,2,3,4-diisopropylidenexylitol represented by the formula (5) is selectively protected and the product is separated from 1,2,4,5-diisopropylidenexylitol represented by the formula (6).

In order to isolate the compound represented by the formula (5) from the mixture of the compounds represented by the formulae (5) and (6) obtained by the acetalization in the step (A1), distillation, column chromatography, and the like can be utilized. However, these structural isomers resemble each other in physical properties such as boiling point and molecular polarity. Therefore, they cannot be efficiently separated by distillation and column chromatography which utilize physical properties and thus a low yield is brought about, so that the method is not suitable for scale-up. On the other hand, when the mixture of the compounds represented by the formulae (5) and (6) is subjected to silyl-etherification, a mixture of compounds represented by the formulae (7) and (8) is obtained. Owing to the difference between the hydroxyl group and the silyl ether group, they are different in molecular polarity to a large extent. Since a physical property such as a boiling point is remarkably changed, the separation from the compound represented by the formula (6) is facilitated and thus efficient purification becomes possible.

The mixture of the compounds represented by the formulae (5) and (6) is reacted using a silicon compound represented by the formula (11) and a tertiary amine to silyl-etherify only the primary hydroxyl group of the compound (5), thereby obtaining the compound represented by the formula (7).

The reaction for the silyl etherification is preferably carried out in the reaction solvent since stirring efficiency decreases with no solvent owing to high viscosity and a silyl etherification ratio decreases. The solvent species is not particularly limited and includes aprotic solvents such as tetrahydrofuran, dimethyl ether, dichloromethane, chloroform, dimethylformamide, toluene, and benzene but more preferred are dichloromethane and chloroform. The amount of the solvent to be used is 1 to 40 weight times, preferably 2 to 20 weight times, and further preferably 3 to 10 weight times the amount of the mixture of the compounds represented by the formulae (5) and (6).

In the silicon compound represented by the formula (11), the halogen atom represented by W includes Cl, Br, and I and is preferably Cl. $R^1$, $R^2$, and $R^3$ represent the same or different hydrocarbon group having 1 to 10 carbon atoms. The hydrocarbon group includes linear or branched alkyl groups having 1 to 10 carbon atoms, linear or branched alkenyl groups having 2 to 10 carbon atoms, linear or branched alkynyl groups having 2 to 10 carbon atoms, aryl groups having 6 to 10 carbon atoms, linear or branched arylalkyl groups having 7 to 10 carbon atoms, linear or branched arylalkenyl groups having 8 to 24 carbon atoms, arylalkynyl groups having 8 to 24 carbon atoms, linear or branched alkylaryl groups having 7 to 10 carbon atoms, and the like.

The silicon compound (11) specifically includes chlorotrimethylsilane, chlorotriethylsilane, chlorotripropylsilane, chlorodimethylisopropylsilane, chlorodimethylethylsilane, chloro-tert-butyldimethylsilane, chloro-tert-butyldiphenylsilane, chlorotriphenylsilane, and the like. More preferred are chloro-tert-butyldimethylsilane, chloro-tert-butyldiphenylsilane, chlorotriphenylsilane, and the like and further preferred is chloro-tert-butyldiphenylsilane.

The amount of the silicone compound (11) to be used is 0.8 to 20 molar equivalents, preferably 0.9 to 10 molar equivalents, and further preferably 1.0 to 5 molar equivalents to the mixture of the compounds represented by the formulae (5) and (6).

As the tertiary amine, it is preferred that anyone selected from the group consisting of dimethylaminopyridine (DMAP), 1,8-diazabicyclo[5,4,0]undec-7-ene (DBU), 1,1,3,3-tetramethylguanidine, 1,5-diazabicyclo[4,3,0]non-5-ene (DABCO), and ethyldiisopropylamine is used singly or is used as a mixture with triethylamine or pyridine. More preferred is DMAP or DBU alone or a mixture of DMAP or DBU and triethylamine and particularly preferred is a mixture of DMAP and triethylamine. The ratio of DBU or DMAP in the mixed base is preferably 5 to 100% by mol, more preferably 5 to 80% by mol, and further preferably 5 to 50% by mol.

The amount of the tertiary amine to be used is 0.9 to 20 molar equivalents, preferably 1.0 to 10 molar equivalents, and further preferably 1.1 to 5 molar equivalents to the mixture of the compounds represented by the formulae (5) and (6). When the tertiary amine is insufficient, an acid to be produced as a by-product as the reaction proceeds cannot be efficiently trapped, so that there is a possibility that the conversion may decrease.

The reaction temperature for the silyl etherification is usually −20 to 80° C., preferably −10 to 60° C. The reaction time is preferably 30 minutes to 24 hours.

A mixture after the reaction contains unreacted compound represented by the formula (6). In the case where the compound represented by the formula (6) remains, it is converted into an impurity having the same molecular weight as that of an objective compound in the polymerization of ethylene oxide in the step (B). Therefore, it is preferred to perform separation and purification at this stage. A method for purification is not particularly limited but it is preferred to separate the unreacted compound represented by the formula (4) by a purification means such as column chromatography, distillation, extraction, or supercritical extraction and purification by distillation is further preferred.

In the case where purification is performed by distillation, it is preferred to separate the compound represented by the formula (6) at 80 to 160° C. at a degree of vacuum of 10 mmHg or lower. When the temperature is higher than 160° C., there is a concern that an impurity produced by elimination of the acetal group owing to high temperature may be formed.

The step (A3) is a step of deprotection of the compound represented by the formula (7) protected in the step (A2), in which 1,2,3,4-diisopropylidenexylitol of the formula (5) with no structural isomer is obtained.

A deprotection reaction of the compound represented by the formula (7) is carried out. The conditions for the deprotection reaction are not particularly limited but the compound represented by the formula (5) can be obtained by a desilylation reaction with a desilylation agent.

A reaction solvent is not particularly limited as far as it is an aprotic solvent. Preferably, tetrahydrofuran, dimethyl ether, dichloromethane, chloroform, dimethylformamide, toluene, benzene, and the like may be mentioned but more preferred is tetrahydrofuran. With no solvent, viscosity of the compound represented by the formula (7) is high, the stirring efficiency decreases, the ratio of desilylation decreases, and thus there is a concern that the compound represented by the formula (7) may remain. The amount of the solvent to be used is 0.4 to 30 times by weight, preferably 0.6 to 20 times by weight, and further preferably 0.8 to 10 times by weight the amount of the compound represented by the formula (7).

As the desilylation agent, an anhydride of tetrabutylammonium fluoride is preferably used but a commercially available mixed solution of tetrabutylammonium fluoride/tetrahydrofuran may be utilized. With a hydrate of tetrabutylammonium fluoride, catalytic action of tetrabutylammonium fluoride is inhibited and there is a concern that the desilylation may not proceed and the compound represented by the formula (7) may remain. Moreover, an acid catalyst such as hydrochloric acid or acetic acid is not preferred since deacetalization takes place together with the desilylation.

The amount of the desilylation agent to be used is 1.0 to 20 molar equivalents, preferably 1.1 to 10 molar equivalents, and further preferably 1.2 to 5 molar equivalents to the compound represented by the formula (7). When the desilylation agent is deficient, the reaction does not completely proceed and the compound represented by the formula (7) remains.

The reaction temperature is preferably 60° C. or lower for suppressing side reactions and is preferably −20° C. or higher for suppressing viscosity increase of the reaction solution. The reaction time is preferably 30 minutes to 24 hours. When it is shorter than 30 minutes, there is a concern that the conversion may be low and when it is longer than 24 hours, there is a concern that a side reaction may take place.

After completion of the reaction, a method for purifying the compound represented by the formula (5) is not particularly limited but it is preferred to perform column chromatography, distillation, extraction, supercritical extraction, or the like and further preferred is column chromatography or distillation. When tetrabutylammonium fluoride of the desilylation agent and tetrabutylammonium salts contained in the formula (5) remain, there is a concern that a catalyst to be used in the next step may be inhibited and thus the conversion may decrease. When the compound represented by the formula (7) remains, there is a concern that it may decompose at the polymerization of ethylene oxide in the step (B) and ethylene oxide as a monomer may be consumed to form a polyoxyethylene impurity. Therefore, there is a need for their removal.

The step (B) comprises the following two steps of (B1) and (B2).

The step (B1) is a step of alcoholation of the compound represented by the formula (5) and either of a step (B1-1) or a step (B1-2) may be used.

In the step (B1-1), metal sodium, metal potassium, or the like is used as a catalyst.

In the step (B1-2), sodium methoxide, potassium t-butoxide, potassium methoxide, or the like is used as a catalyst.

The step (B2) is a step of addition polymerization of ethylene oxide at a reaction temperature of 50 to 130° C.

In the step (B1-1), metal sodium or metal potassium, preferably metal sodium is used as a catalyst and is dissolved in a catalyst amount of 5 to 50% by mol at 10 to 50° C.

With regard to the catalyst amount in the step (B1-1), since the polymerization rate of ethylene oxide decreases at less than 5% by mol and impurities such as a terminal vinyl ether compound are produced due to a long-term high temperature reaction, the use of the catalyst in an amount of 5% by mol or more is advantageous in the production of a high quality high-molecular-weight compound. When the catalyst amount exceeds 50% by mol, the viscosity of the reaction liquid increases or the liquid solidifies at the alcoholation reaction and thus there is a tendency that the stirring efficiency decreases and the alcoholation is not accelerated. Moreover, when the liquid solidifies, handling thereof tends to be difficult, which causes water absorption. When the alcoholate has absorbed water, a polyalkylene glycol compound derived from water is formed and is contained as an impurity undesirable in medical uses.

When the temperature at the dissolution is higher than 50° C., a decomposition reaction may occur to form methanol and xylitol. When methanol is formed, it initiates addition polymerization with ethylene oxide as in the case of the target compound, whereby an impurity having a molecular weight the same as the molecular weight of the target compound. When the impurity derived from methanol is formed, a functional group is introduced through functionalization in the subsequent step (C) as in the case of the target compound, so that the impurity is converted into an impurity which is capable of reacting with a bio-related substance. Moreover, when xylitol is formed, it also initiates addition polymerization with ethylene oxide to form a high-molecular-weight impurity having a molecular weight 5 times that of the target compound. Since plural functional groups are introduced to the high-molecular-weight impurity through functionalization in the subsequent step (C), the impurity is converted into an impurity which is plurally capable of reacting with a bio-related substance. A polyoxyethylene derivative containing these impurities is not desirable in a medical use where a highly pure product is required.

When the dissolution is carried out at a temperature lower than 10° C., like the case that the catalyst amount is more than 50% by mol, the viscosity of the reaction liquid increases or the liquid solidified at the alcoholation reaction, handling thereof tends to be difficult, and water absorption is caused.

The reaction solvent to be used in the alcoholation reaction is not particularly limited as far as it is an aprotic solvent such as toluene, benzene, xylene, acetonitrile, tetrahydrofuran, dimethyl sulfoxide, dimethylformamide, or dimethylacetamide, but preferable is toluene or no solvent. The reaction time is preferably 1 to 24 hours. When the time is less than 1 hour, there is a possibility that the catalyst does not completely dissolved. When the time is longer than 24 hours, there is a possibility that the above decomposition reaction occurs.

In the step (B1-2), sodium methoxide, potassium t-butoxide, or potassium methoxide, preferably sodium methoxide is added in an amount of 5-50% by mol and is reacted at 20 to 80° C. On this occasion, an operation of reducing pressure may be conducted so as to accelerate the exchange reaction.

The amount of the catalyst is preferably an amount of 5 to 50% by mol for the aforementioned reason. With regard to the reaction temperature, when the temperature is lower than 20° C., the conversion of the exchange reaction decreases, an alcohol such as methanol remains, and an impurity having a molecular weight equal to that of the target compound is formed through the addition polymerization of ethylene oxide. When the temperature is higher than 80° C., a decomposition reaction occurs. Since the decomposition reaction tends to occur in the alcoholation reaction, the reaction time is desirably 1 to 3 hours. The reaction solvent is not particularly limited as far as it is an aprotic solvent but is preferably toluene or no solvent.

In the step (B2), ethylene oxide is subjected to addition polymerization at a reaction temperature of 50 to 130° C. to obtain the compound of the formula (8) (polyoxyethylene derivative (8)). With regard to the reaction temperature, when the temperature is lower than 50° C., the polymerization rate is low and there is a tendency to decrease the quality of the compound of the formula (8). Moreover, when the temperature is higher than 130° C., side reactions such as vinyl etherification of the terminal end occur during the polymerization and thus the quality of the target compound tends to decrease. During the polymerization, as the molecular weight increases, the viscosity of the reaction solution also increases, so that an aprotic solvent, preferably toluene may be optionally added.

The step (C) is a step of functionalizing the hydroxyl group at the terminal end of the compound of the formula (8) (polyoxyethylene derivative (8)). Depending on the kind of the functional group, deacetalization of the step (D) can be performed at the functionalization simultaneously.

Using the hydroxyl group at the terminal end of the compound of the formula (8) (polyoxyethylene derivative (8)), it is possible to manufacture the polyoxyethylene derivative represented by the formula (9) by modifying the hydroxyl group to each of various functional groups shown in the groups (II), (III), (IV), (V), (VI), and (VII).

Moreover, using a compound having each of the functional groups of the groups (II), (III), (IV), (V), (VI), and (VII) as an intermediate, functionalization can be performed by further reacting the compound with the other compound. For example, using an intermediate having a functional group of (k) as a raw material, the functional groups of (a) and (d) can be obtained.

The following will describe a method for synthesizing the polyoxyethylene derivative represented by the formula (9) (polyoxyethylene derivative (9)) in detail.

[Method for Introducing Functional Groups (b) and (e)]

By reacting the compound (8) with an organic base such as triethylamine, pyridine, or 4-dimethylaminopyridine or an inorganic base such as sodium carbonate, sodium hydroxide, sodium hydrogen carbonate, sodium acetate, potassium carbonate, or potassium hydroxide and any one of the compounds represented by the following formulae (b1) and (e1) (compound (b1) and compound (e1)) in an aprotic solvent such as toluene, benzene, xylene, acetonitrile, ethyl acetate, diethyl ether, t-butyl methyl ether, tetrahydrofuran, chloroform, dichloromethane, dimethyl sulfoxide, dimethylformamide, or dimethylacetamide or without any solvent, functional groups (b) and (e) can be introduced, respectively (compound (b) or (e) into which the functional group (b) or (e) has been introduced is obtained). The ratio of the organic base or inorganic base to be used is not particularly limited but is preferably equimolar or more to the compound (8). Furthermore, an organic base may be used as a solvent. $W^2$ in the formula (b1) or (e1) is a halogen atom selected from Cl, Br and I, and is preferably Cl. The ratio of the compounds (b1) and (e1) to be used is not particularly limited but is preferably equimolar or more and more preferably, the compounds are reacted in the range of equimolar to 50 molar equivalents to the compound (8). The reaction temperature is preferably 0 to 300° C., more preferably 20 to 150° C. The reaction time is preferably 10 minutes to 48 hours, more preferably 30 minutes to 24 hours. The compound formed may be purified by a purification means such as extraction, recrystallization, adsorption treatment, reprecipitation, column chromatography, or supercritical extraction.

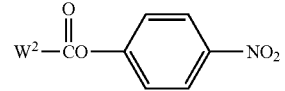

(b1)

-continued

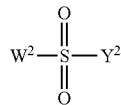
(e1)

wherein $W^2$ is a halogen atom selected from Cl, Br, and I and $Y^2$ represents a hydrocarbon group having 1 to 10 carbon atoms which may contain a fluorine atom.

[Method for Introducing Functional Group (f)]

A carboxyl body (f) into which the functional group (f) has been introduced can be obtained by reacting the compound (8) or an amine (k) to be mentioned later with a dicarboxylic acid anhydride such as succinic anhydride or glutaric anhydride. The reaction of the compound (8) or the amine (k) with the dicarboxylic acid anhydride is carried out in the aforementioned aprotic solvent or without any solvent. The ratio of the dicarboxylic acid anhydride to be used is not particularly limited but is preferably equimolar or more, more preferably equimolar to molar equivalents to the compound (8). The reaction temperature is preferably 0 to 200° C., more preferably 20 to 150° C. The reaction time is preferably 10 minutes to 48 hours, more preferably 30 minutes to 12 hours. In the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 50% by weight, more preferably 0.5 to 20% by weight. The carboxyl body (f) thus formed may be purified by a purification means such as extraction, recrystallization, adsorption treatment, reprecipitation, column chromatography, or supercritical extraction or, in the case where it is used as a raw material for a condensation reaction, it may be used as it is.

The carboxyl body (f) can be obtained by reacting the compound (8) with a halogenated alkyl ester such as ethyl 6-bromohexanoate or ethyl 7-bromoheptanoate. The etherification reaction of the compound (8) with a halogenated alkyl ester is carried out in the aforementioned aprotic solvent or without any solvent. The ratio of the halogenated alkyl ester to be used is not particularly limited but is preferably equimolar or more, more preferably equimolar to 30 molar equivalents to the compound (8). The reaction temperature is preferably 0 to 200° C., more preferably 20 to 150° C. The reaction time is preferably 10 minutes to 48 hours, more preferably 30 minutes to 12 hours. In the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 500% by weight, more preferably 0.5 to 300% by weight. After the etherification, hydrolysis of the ester is carried out by adding an aqueous solution of sodium hydroxide, potassium hydroxide, or the like in the case of the organic base or water in the case of the inorganic base. The reaction temperature is preferably 0 to 100° C., more preferably 20 to 100° C. The reaction time is preferably 10 minutes to 48 hours, more preferably 30 minutes to 12 hours. After the reaction, neutralization is performed with hydrochloric acid, sulfuric acid, or the like. The carboxyl body (f) thus formed may be purified by a purification means such as extraction, recrystallization, adsorption treatment, reprecipitation, column chromatography, or supercritical extraction or, in the case where it is used as a raw material for a condensation reaction, it may be used as it is.

[Process for Introducing Functional Group (a)]

A succinimide body (a) into which the functional group (a) has been introduced can be obtained by subjecting the carboxyl body (f) to a condensation reaction with N-hydroxysuccinimide in the presence of a condensing agent such as dicyclohexylcarbodiimide (DCC) or 1-ethyl-3-(3-dimethylaminopropyl)carbodiimide hydrochloride (EDC). Such a condensation reaction is carried out in the aforementioned aprotic solvent or without any solvent. The condensing agent is not particularly limited but is preferably DCC. The ratio of DCC to be used is preferably equimolar or more, more preferably equimolar to 5 molar equivalents to the carboxyl body (f). The ratio of N-hydroxysuccinimide to be used is preferably equimolar or more, more preferably equimolar to 5 molar equivalents to the carboxyl body (f). The reaction temperature is preferably 0 to 100° C., more preferably 20 to 80° C. The reaction time is preferably 10 minutes to 48 hours, more preferably 30 minutes to 12 hours. The succinimide body (a) formed may be purified by a purification means such as extraction, recrystallization, adsorption treatment, reprecipitation, column chromatography, or supercritical extraction.

Also, the succinimide body (a) can be obtained by reacting the compound (8) with N,N'-disuccinimide carbonate. The reaction is carried out in an aforementioned aprotic solvent or in no solvent as mentioned above. The ratio of the N,N'-disuccinimide carbonate to be used is preferably equimolar or more, further preferably equimolar to 5 molar equivalents to the compound (8). The reaction temperature is preferably 0 to 100° C., further preferably 20 to 80° C. The reaction time is 10 minutes to 48 hours, further preferably 30 minutes to 12 hours. The formed compound may be purified by a purification means such as extraction, recrystallization, adsorption treatment, reprecipitation, column chromatography, or supercritical extraction.

[Process for Introducing Functional Group (k)]

An amine body (k) having the functional group (k) can be obtained by adding the compound (8) to acrylonitrile or the like in a solvent such as water or acetonitrile using an inorganic base such as sodium hydroxide or potassium hydroxide as a catalyst to obtain a nitrile body and then carrying out a hydrogenation reaction of the nitrile group under a nickel or palladium catalyst in an autoclave. The ratio of the inorganic base to be used when the nitrile body is obtained is not particularly limited but is preferably 0.01 to 50% by weight relative to the compound (8). The ratio of acrylonitrile or the like to be used is not particularly limited but is preferably 0.5 to 5 times by weight the weight of the compound (8) and further preferably, it is preferred to carry out the reaction in the range of 1 to 4 times by weight. Also, acrylonitrile may be used as a solvent. The reaction temperature is preferably –50 to 100° C., further preferably –20 to 60° C. The reaction time is 10 minutes to 48 hours, further preferably 30 minutes to 24 hours. A reaction solvent in the subsequent hydrogenation reaction of the nitrile body is not particularly limited as far as it is a solvent which is not involved in the reaction but is preferably toluene. The ratio of the nickel or palladium catalyst to be used is not particularly limited but is 0.05 to 30% by weight, preferably 0.5 to 20% by weight relative to the nitrile body. The reaction temperature is preferably 20 to 200° C., further preferably 50 to 150° C. The reaction time is 10 minutes to 48 hours, further preferably 30 minutes to 24 hours. A hydrogen pressure is preferably 2 to 10 MPa, further preferably 3 to 8 MPa. Moreover, in order to prevent dimerization, ammonia may be added into the reaction system. An ammonia pressure in the case of adding ammonia is not particularly limited but is 0.1 to 10 MPa, further preferably 0.3 to 2 MPa. The formed compound may be purified by an aforementioned purification means.

The amine body (k) can be also obtained by reacting the compound (e) with aqueous ammonia. The reaction is carried out in aqueous ammonia and the concentration of ammonia is not particularly limited but is preferably in the range of 10 to 40% by mass. The ratio of the aqueous ammonia to be used is preferably 1 to 300 times the weight of the compound (e). The reaction temperature is preferably 0 to 100° C., further preferably 20 to 80° C. The reaction time is preferably 10 minutes to 72 hours, further preferably 1 to 36 hours. Moreover, the amine body (k) can be also obtained by reacting the compound (e) with ammonia in an autoclave. A reaction solvent is not particularly limited but preferably includes methanol and ethanol. The amount of ammonia is preferably 10 to 300% by weight, further preferably 20 to 200% by weight relative to the compound (e). The reaction temperature is preferably 50 to 200° C., further preferably 80 to 150° C. The reaction time is preferably 10 minutes to 24 hours, further preferably 30 minutes to 12 hours. The formed compound may be purified by an aforementioned purification means.

Also, the amine body (k) can be obtained by bonding the compound (8) to phthalimide in an aprotic solvent by Mitsunobu reaction, followed by deprotection with a polyfunctional amine. The reaction conditions for Mitsunobu reaction are not particularly limited but chloroform or dichloromethane is preferred as the reaction solvent. Moreover, it is preferred to use triphenylphosphine in an amount of equimolar or more, preferably equimolar to 50 molar equivalents to the compound (8) and diisopropyl azodicarboxylate in an amount of equimolar or more, preferably equimolar to 50 molar equivalents to the compound (8). The reaction temperature is preferably 0 to 100° C., further preferably 10 to 50° C. The reaction time is preferably 10 minutes to 72 hours, further preferably 30 minutes to 6 hours.

For deprotection, a polyfunctional amine such as hydrazine or ethylenediamine is preferably used in an amount of equimolar or more, preferably equimolar to 500 molar equivalents to the compound (8). A reaction solvent is not particularly limited but methanol is preferred. The reaction temperature is preferably 0 to 100° C., further preferably 20 to 80° C. The reaction time is preferably 10 minutes to 72 hours, further preferably 1 to 10 hours. The formed compound may be purified by a purification means such as extraction, recrystallization, adsorption treatment, reprecipitation, column chromatography, or supercritical extraction.

[Process for Introducing Functional Group (d)]

A maleimide body (d) having the functional group (d) can be obtained by reacting the amino group of the amine body (k) obtained by the aforementioned method with maleic anhydride in the aforementioned aprotic solvent or without any solvent to obtain a maleimide body and then subjecting it to a ring closure reaction using acetic anhydride and sodium acetate as a catalyst. The ratio of maleic anhydride to be used in the maleimidation reaction is not particularly limited but is preferably equimolar or more, more preferably equimolar to 5 molar equivalents to the amine body (k). The reaction temperature is preferably 0 to 200° C., more preferably 20 to 120° C. The reaction time is preferably 10 minutes to 48 hours, more preferably 30 minutes to 12 hours. The maleimide body (d) formed may be purified by the aforementioned purification means or may be used as it is in the next ring closure reaction.

A reaction solvent in the subsequent ring closure reaction is not particularly limited but is preferably an aprotic solvent or acetic anhydride. The ratio of sodium acetate to be used is not particularly limited but is preferably equimolar or more, more preferably equimolar to 50 molar equivalents to the maleimide body (d). The reaction temperature is preferably 0 to 200° C., more preferably 20 to 150° C. The reaction time is preferably 10 minutes to 48 hours, more preferably 30 minutes to 12 hours. The formed compound may be purified by the aforementioned purification means.

The above maleimide body (d) can be also obtained by reacting the compound (d1) represented by the following formula (d1) with the aforementioned amine body (k). The reaction is carried out in the aforementioned aprotic solvent or without any solvent and the compound (d1) is added in an amount of equimolar or more to the amino group of the amine body (k) and reacted. The ratio of the compound (d1) to be used is preferably equimolar or more, more preferably equimolar to 5 molar equivalents to the amino group of the amine body (k). The reaction temperature is preferably 0 to 200° C., more preferably 20 to 80° C. The reaction time is preferably 10 minutes to 48 hours, more preferably 30 minutes to 12 hours. During the reaction, light shielding may be conducted. The formed compound may be purified by the aforementioned purification means.

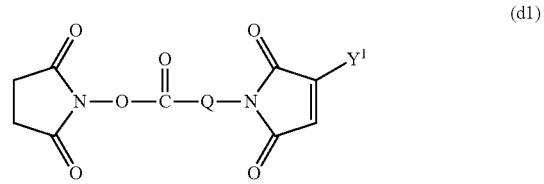

(d1)

wherein Q represents a hydrocarbon group having 1 to 9 carbon atoms and $Y^1$ represents a hydrogen atom or a hydrocarbon having 1 to 5 carbon atoms.

[Method for Introducing Functional Group (i)]

The functional group (i) can be obtained by reacting the amine body (k) obtained by the method as mentioned above with iodoacetic anhydride in an aforementioned aprotic solvent or without any solvent. The ratio of iodoacetic anhydride to be used is not particularly limited but is preferably equimolar or more, further preferably equimolar to 5 molar equivalents to the amino group of the amine body (k). The reaction temperature is preferably 0 to 200° C., further preferably 20 to 120° C. The reaction time is preferably 10 minutes to 48 hours, further preferably 30 minutes to 12 hours. The formed compound (i) having the functional group (i) may be purified by a purification means such as extraction, recrystallization, adsorption treatment, reprecipitation, column chromatography, or supercritical extraction.

Also, the functional group (i) can be obtained by subjecting the amine body (k) to a condensation reaction with iodoacetic acid in the presence of a condensing agent such as DCC or EDC. The condensation reaction is also carried out in an aforementioned aprotic solvent or without any solvent as mentioned above. The condensing agent is not particularly limited but is preferably DCC. The ratio of DCC to be used is preferably equimolar or more, further preferably equimolar to 5 molar equivalents to the amine body (k). The ratio of iodoacetic acid to be used is preferably equimolar or more, further preferably equimolar to 5 molar equivalents to the amine body (k). The reaction temperature is preferably 0 to 100° C., further preferably 20 to 80° C. The reaction time is 10 minutes to 48 hours, further preferably 30 minutes to 12 hours. The formed compound may be purified by an aforementioned purification means.

[Method for Introducing Functional Group (l)]

An oxyphthalimide body into which an oxyphthalimido group has been introduced can be obtained by reacting the carbonate body (b) with the compound represented by the following formula (l1) (compound (l1)) in the presence of an alkali catalyst such as triethylamine or pyridine. The reaction can be carried out under no solvent or under a polar solvent. The solvent is not particularly limited but is preferably methanol. The ratio of the alkali catalyst to be used is not particularly limited but is preferably equimolar or more, further preferably equimolar to 20 molar equivalents to the carbonate body (b). The ratio of the compound (l1) to be used is preferably equimolar or more, further preferably equimolar to 20 molar equivalents to the carbonate body (b). The reaction temperature is preferably 0 to 100° C., further preferably 20 to 80° C. The reaction time is preferably 10 minutes to 48 hours, further preferably 30 minutes to 12 hours. The formed compound may be purified by a purification means such as extraction, recrystallization, adsorption treatment, reprecipitation, column chromatography, or supercritical extraction or may be used in the next step without purification.

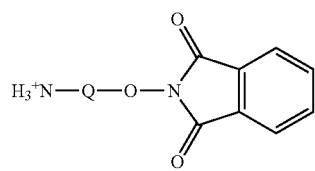

(l1)

wherein Q represents a hydrocarbon group having 1 to 9 carbon atoms.

The oxyphthalimide body can be also obtained by bonding the compound (8) to hydroxyphthalimide in an aprotic solvent by Mitsunobu reaction, followed by deprotection with a polyfunctional amine. The reaction conditions for Mitsunobu reaction are not particularly limited but chloroform or dichloromethane is preferred as the reaction solvent. Moreover, it is preferred to use triphenylphosphine in an amount of equimolar or more, preferably equimolar to 50 molar equivalents to the compound (8) and diisopropyl azodicarboxylate in an amount of equimolar or more, preferably equimolar to 50 molar equivalents to the compound (8). The reaction temperature is preferably 0 to 100° C., further preferably 10 to 50° C. The reaction time is preferably 10 minutes to 72 hours, further preferably 30 minutes to 6 hours.

An oxyamine body (l) into which the functional group (l) has been introduced can be obtained by reacting the oxyphthalimide body obtained by any of these methods in the presence of a polyfunctional amine such as hydrazine or ethylenediamine.

A reaction solvent is not particularly limited but is preferably methanol, dichloromethane, or water. The ratio of the polyfunctional amine to be used is not particularly limited but is preferably equimolar or more, further preferably equimolar to 50 molar equivalents to the oxyphthalimide body. The reaction temperature is preferably 0 to 100° C., further preferably 20 to 80° C. The reaction time is preferably 10 minutes to 48 hours, further preferably 30 minutes to 12 hours. The formed compound may be purified by a purification means such as extraction, recrystallization, adsorption treatment, reprecipitation, column chromatography, or supercritical extraction.

[Process for Introducing Functional Group (c)]

An aldehyde body (c) having the functional group (c) can be obtained by reacting the compound (e) with an acetal compound represented by the following formula (c1) (compound (c1)) to obtain an acetal compound and then subjecting it to hydrolysis under an acidic condition. The acetalization reaction can be achieved by reacting the compound (e) with an equimolar or more amount, preferably an equimolar to 50 molar amount of the compound (c1) in the aforementioned aprotic solvent or without any solvent. The compound (c1) can be prepared from the corresponding alcohol using metal sodium, metal potassium, sodium hydride, potassium hydride, sodium methoxide, potassium t-butoxide, or the like. The reaction temperature is preferably 0 to 300° C., more preferably 20 to 150° C. The reaction time is preferably 10 minutes to 48 hours, more preferably 30 minutes to 24 hours.

In the case of using the compound represented by the following formula (c2) (compound (c2)), an acetal body can be obtained by converting the hydroxyl group of the compound (8) into an alcoholate by the aforementioned method and then reacting it with the compound (c2) in a ratio of equimolar or more, preferably equimolar to 100 molar equivalents in the aforementioned aprotic solvent or without any solvent. The reaction temperature is preferably 0 to 300° C., more preferably 20 to 150° C. The reaction time is preferably 10 minutes to 48 hours, more preferably 30 minutes to 24 hours.

In the case of using the compound represented by the following formula (c3) (compound (c3)), an acetal body can be obtained by reacting the compound into which the aforementioned functional group (a), (b), (e), or (f) has been introduced (compound (a), (b), (e), or (f)) with the compound (c3). A solvent for the reaction is not particularly limited but the reaction is preferably carried out in the aforementioned aprotic solvent. The charging ratio of the compound (c3) is preferably equimolar or more, more preferably equimolar to 10 molar equivalents to the compound (a), (b), (e), or (f). The reaction temperature is preferably −30 to 200° C., more preferably 0 to 150° C. The reaction time is preferably 10 minutes to 48 hours, more preferably 30 minutes to 24 hours. In the case of using the compound (f), a condensing agent such as DCC or EDC may be optionally used. Any acetalization reaction may be carried out under light shielding. The acetal body thus obtained may be purified by the aforementioned purification means or may be used as it is in the next aldehyde-formation reaction.

The aldehyde body (c) can be obtained by hydrolyzing the acetal body in a 0.1 to 50% aqueous solution which is adjusted to pH 1 to 4 with an acid such as acetic acid, phosphoric acid, sulfuric acid, or hydrochloric acid. The reaction temperature is preferably −20 to 100° C., more preferably 0 to 80° C. The reaction time is preferably 10 minutes to 24 hours, more preferably 30 minutes to 10 hours. The reaction may be carried out under light shielding. The formed compound may be purified by the aforementioned purification means. Moreover, in the aldehyde formation, it is possible to perform deacetalization of the step (D) simultaneously.

(c1)

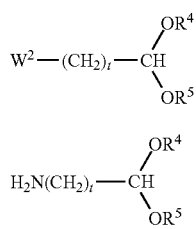

(c2)

(c3)

wherein $R^4$ and $R^5$ each independently represent a hydrocarbon group having 1 to 3 carbon atoms and may be the same or different from each other, and they may together form a ring; M is sodium or potassium; $W^2$ is a halogen atom selected from Cl, Br, and I; and t is an integer of 1 to 5.

[Process for Introducing Functional Group (g)]

A mercapto body having the functional group (g) (compound (g)) can be obtained by reacting the compound (e) with a thio-formation agent such as thiourea. The compound (e) is manufactured as mentioned above. The thio-formation reaction is carried out in a solvent such as water, an alcohol, or acetonitrile or without any solvent. The ratio of thiourea to be used is equimolar or more, more preferably equimolar to 50 molar equivalents to the compound (e). The reaction temperature is preferably 0 to 300° C., more preferably 20 to 150° C. The reaction time is preferably 10 minutes to 48 hours, more preferably 30 minutes to 24 hours. After the reaction, the mercapto body can be obtained by subjecting the formed thiazolium salt to alkali hydrolysis. The formed compound may be purified by the aforementioned purification means. Moreover, in the mercapto formation, it is possible to perform deacetalization of the step (D) simultaneously in the pH adjustment after hydrolysis.

Moreover, the above mercapto body can be also obtained by reacting the compound (e) with a compound represented by the following formula (g1) (compound (g1)), followed by decomposition with a primary amine. The reaction of (e) with (g1) is carried out in the aforementioned aprotic solvent or without any solvent. The ratio of the compound (g1) to be used is equimolar or more, more preferably equimolar to 50 molar equivalents to the compound (e). The reaction temperature is preferably 0 to 300° C., more preferably 20 to 80° C. The reaction time is preferably 10 minutes to 48 hours, more preferably 30 minutes to 24 hours. The subsequent alkali decomposition with a primary amine is carried out in the aforementioned aprotic solvent or without any solvent. The primary amine to be used is not particularly limited but preferably includes ammonia, methylamine, ethylamine, propylamine, butylamine, pentylamine, hexylamine, cyclohexylamine, ethanolamine, propanolamine, butanolamine, and the like. Naturally, the primary amine may be used as a solvent. The formed compound may be purified by the aforementioned purification means.

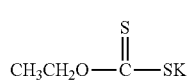

(g1)

[Process for Introducing Functional Group (h)]

A compound having the functional group (h) (compound (h)) can be obtained by reacting the compound (g) with 2,2-dipyridyl disulfide. In the reaction, a solvent is not particularly limited but the reaction is preferably carried out in an alcohol. The ratio of 2,2-dipyridyl disulfide to be charged relative to the compound (g) is preferably equimolar or more, further preferably equimolar to 50 molar equivalents. The reaction temperature is preferably −30 to 100° C., further preferably 0 to 60° C. The reaction time is preferably 10 minutes to 48 hours, further preferably 30 minutes to 24 hours. The thus obtained acetal body may be purified by an aforementioned purification means.

[Process for Introducing Functional Group (m)]

The compound having the functional group (m) (compound (m)) can be obtained by reacting the aforementioned compound (a), (b), (c), or (e) with tert-butyl carbazinate in an aforementioned aprotic solvent or with no solvent and deprotecting the tert-butoxycarbonyl group (Boc group). The ratio of tert-butyl carbazinate to be used is not particularly limited but is preferably equivalent mole or more, further preferably equivalent mole to 10 moles relative to the compound (a), (b), (c), or (e). The reaction temperature is preferably 0 to 200° C., further preferably 20 to 80° C. The reaction time is preferably 10 minutes to 48 hours, further preferably 30 minutes to 12 hours. The formed (m) body may be purified by an aforementioned purification means. Moreover, at the deprotection of the Boc group, it is possible to perform deacetalization of the step (D) simultaneously.

[Method for Introducing Functional Group (j)]

An acetylene compound represented by the following formula (j) (compound (j)) can be obtained by reacting the aforementioned compound (a), (b), (c), or (e) with an acetylene compound represented by the following formula (j1) (compound (j1)). The acetylene-forming reaction can be attained by reacting the compound (j1) in an amount of equimolar or more, preferably equimolar to 50 molar equivalents to the compound (a), (b), (c), or (e) in a protic solvent or without any solvent. The reaction temperature is preferably 0 to 300° C., further preferably 20 to 150° C. The reaction time is preferably 10 minutes to 48 hours, further preferably 30 minutes to 24 hours. The formed compound may be purified by an aforementioned purification means.

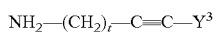

(j1)

wherein t is an integer of 1 to 5 and $Y^3$ represents a hydrogen atom or a hydrocarbon group having 1 to 5 carbon atoms.

[Method for Introducing Functional Group (n)]

An azide compound having the functional group (n) (compound (n)) can be obtained by reacting the amine body (k) obtained by the method as mentioned above with the compound represented by the following formula (n1) (compound (n1)) in the presence of a condensing agent such as DCC or EDC. The condensation reaction is carried out in an aforementioned aprotic solvent or without any solvent. The condensing agent is not particularly limited but is preferably DCC. The ratio of DCC to be used is preferably equimolar or more, further preferably equimolar to 5 molar equivalents to the amine body (k). The ratio of the compound (n1) to be used is preferably equimolar or more, further preferably equimolar to 5 molar equivalents to the compound (k). The reaction temperature is preferably 0 to 100° C., further preferably 20 to 80° C. The reaction time is 10 minutes to 48 hours, further preferably 30 minutes to 12 hours. The formed compound may be purified by an aforementioned purification means.

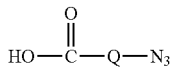

(n1)

wherein Q represents a hydrocarbon group having 1 to 9 carbon atoms.

The step (D) is a deprotection step of cleaving the cyclic acetal structure of the polyoxyethylene derivative represented by the formula (9) having a functional group (hereinafter also referred to as "compound (9)"). Depending on the kind of the functional group, functionalization can be further performed after the deacetalization in the step (D).

A method of deprotection of the cyclic acetal structure is not particularly limited as far as it is a common deprotection method as described in PROTECTIVE GROUPS IN ORGANIC SYNTHESIS (THEODORA W. GREENE et al) and the like. Specifically, the protection can be performed in the presence of an acid catalyst. The acid catalyst includes acetic acid, hydrochloric acid, phosphoric acid, p-toluene-sulfonic acid, or the like and preferred are hydrochloric acid and phosphoric acid and more preferred is phosphoric acid.

The amount of the acid to be used is preferably 0.05 to 2 times by weight, more preferably 0.1 to 1 time by weight the amount of the compound (9). A solvent to be used for the deprotection reaction is water, methanol, ethanol, acetonitrile, tetrahydrofuran, dioxane, dimethylsulfoxide, dimethylformamide, or dimethylacetimide and preferred is water or methanol. The amount of the solvent to be used is 1 to 50 times by weight, preferably 2 to 35 times by weight, and further preferably 5 to 20 times by weight the amount of the compound (8).

The reaction time is preferably 1 to 24 hours. When the time is shorter than 1 hour, the deprotection reaction proceeds insufficiently. When the time is longer than 24 hours, there is a concern that oxidative decomposition of polyoxyethylene by an acid and deactivation of the functional group may occur. The reaction temperature is usually 0 to 60° C., preferably 10 to 40° C.

After the deprotection, the product may be purified by a purification means such as extraction, recrystallization, adsorption treatment, reprecipitation, column chromatography, or supercritical extraction. Preferably, the compound (9) can be obtained by conducting recrystallization and drying the resulting crystals under reduced pressure.

After the deacetalization in the step (D), functionalization can be further conducted. It is desirable to conduct the functionalization after the step (D) for the functional group which may be reacted or decomposed under the deacetalization conditions.

The polyoxyethylene derivative (1) of the invention can be also manufactured by the manufacturing method shown in the following process drawing (process drawing III).

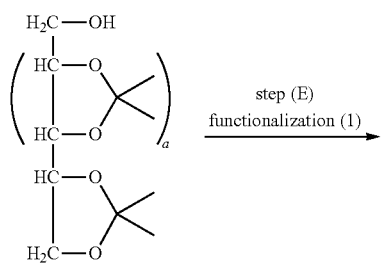

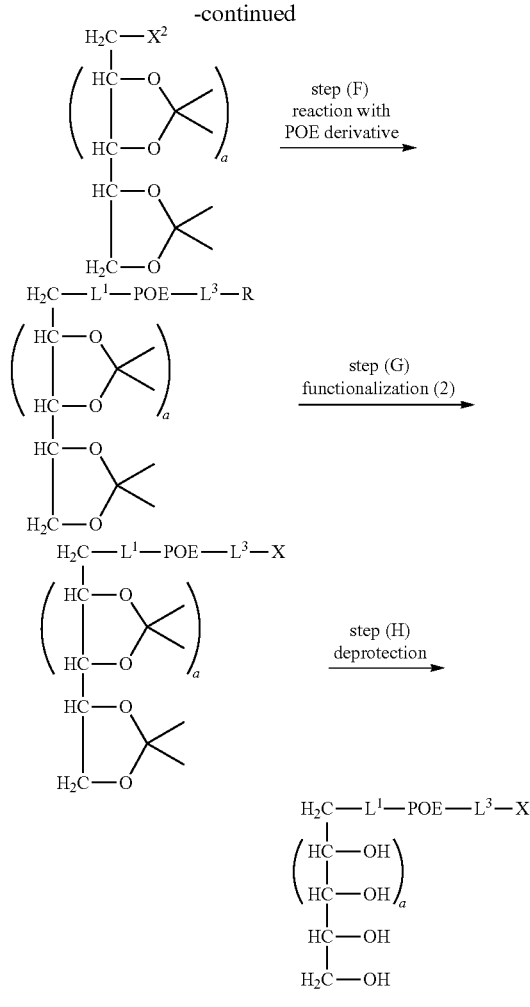

wherein POE, $L^1$, $L^3$, X, and a have the same meanings as mentioned above; R represents a functional group protected with a protective group or a hydroxyl group which may be protected, and $X^2$ represents an amino group, an activated carbonate group, or an activated sulfonate group.

The step (E) is a step of converting the remaining hydroxyl group of the protected polyhydric alcohol derivative into a functional group.

The step (F) is a step of bonding the protected polyhydric alcohol derivative functionalized in the step (E) to the polyoxyethylene derivative through reaction.

The step (G) is a step of performing functionalization through deprotection of R that is a protective group. If necessary, the functionalization can be also conducted in accordance with the step (C) in the aforementioned step drawings I and II. Depending on the kind of the protective group of R at the polyoxyethylene terminal end, it is possible to perform deacetalization of the subsequent step simultaneously with the functionalization.

The step (H) is a step of cleaving the cyclic acetal structure. Four hydroxyl groups are produced in the case of a=1 and six hydroxyl groups are produced in the case of a=2. Depending on the kind of the functional group X at the polyoxyethylene terminal end, functionalization can be further performed after the step (H).

By performing the above steps (E), (F), (G), and (H), the polyoxyethylene derivative represented by the formula (2b) (polyoxyethylene derivative (2b)) is manufactured.

The following will further describe preferable specific examples of the method for manufacturing the polyoxyethylene derivative (2b). Since the derivative can be manufactured by the same manufacturing method in both cases of a=1 and a=2, the derivative of a=1, i.e., the polyoxyethylene derivative represented by the following formula (15) (polyoxyethylene derivative (15)) will be described.

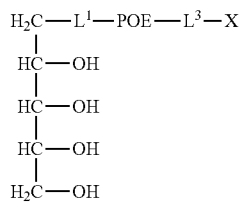

(15)

wherein POE, $L^1$, $L^3$, and X have the same meanings as mentioned above.

The polyoxyethylene derivative (15) can be manufactured by the route shown in the following process drawing (process drawing IV).

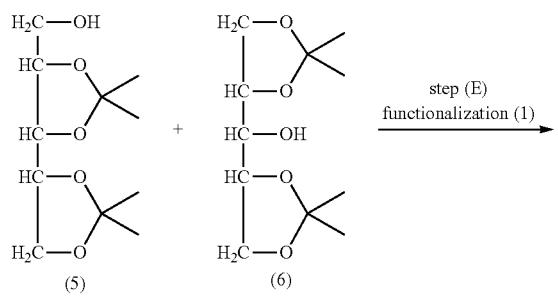

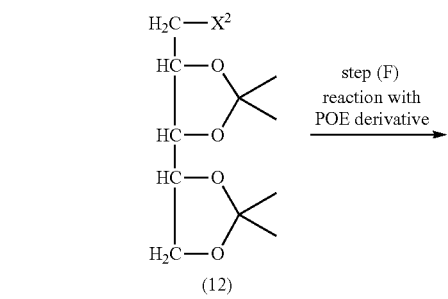

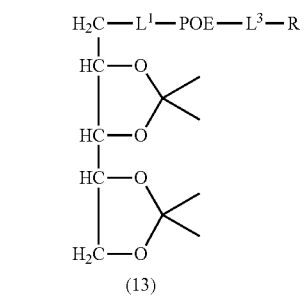

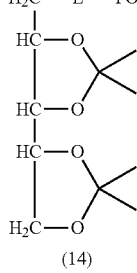

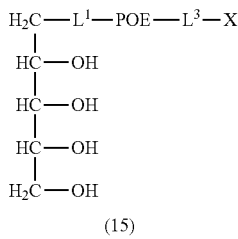

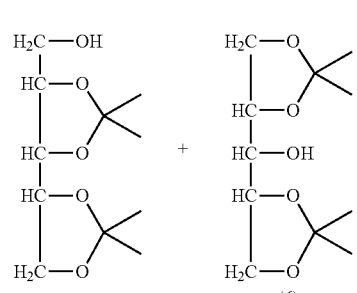

(15)

wherein $R^1$, $R^2$, and $R^3$ each independently represent a hydrocarbon group having 1 to 10 carbon atoms; W represents a halogen atom; and POE, $L^3$, and X have the same meanings as mentioned above. wherein POE, $L^1$, $L^3$, R, $X^2$, and X have the same meanings as mentioned above.

In the above process drawing, the compound (15) corresponds to the compound represented by the formula (2b).

The step (E) is a step for functionalizing the mixture of the compounds represented by the formulae (5) and (6) to obtain the compound of the formula (12) containing no structural isomer. For the step (E), either the following step (E1) or (E2) may be used.

The step (E1) comprises two steps of the following (E1-1) and (E1-2).

The step (E1-1) is a step of selectively converting only one of structural isomers into a phthalimide and separating it from another isomer. Only the primary hydroxyl group of 1,2,3,4-diisopropylidenexylitol represented by the formula (5) is selectively converted into a phthalimido group and the product is separated from 1,2,4,5-diisopropylidenexylitol represented by the formula (6).

The step (E1-2) is a deprotection step of the phthalimido group.

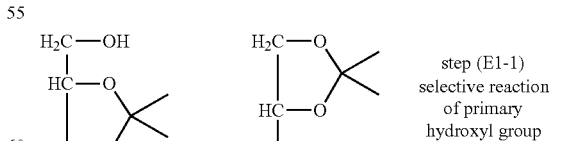

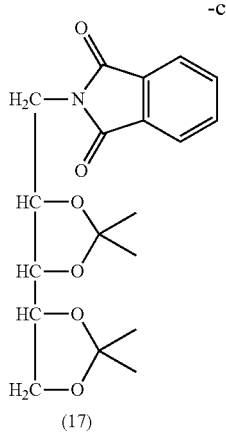

In the above process drawing, the compound (17) corresponds to the compound represented by the formula (12).

In the step (E1-1), the mixture of the compounds represented by the formulae (5) and (6) is reacted with phthalimide to convert only the primary hydroxyl group of the compound (5) into a phthalimido group, thereby obtaining a compound represented by the formula (17).

For the phthalimide formation, it is preferred to remove water in the reaction system by azeotropic dehydration before the reaction. A solvent to be used is not particularly limited as far as it is an aprotic solvent capable of azeotropic dehydration but is preferably toluene, xylene, or cyclohexene and further preferably toluene. The amount of the solvent is 1 to 10 times by weight, preferably 2 to 6 times by weight, and further preferably 3 to 5 times by weight the amount of the mixture.

After the mixture of the compounds represented by the formulae (5) and (6) is dissolved in an organic solvent capable of azeotropic dehydration, the solvent is refluxed and removed by distillation in an amount of 5 to 75% by weight, preferably 10 to 50% by weight based on the charged amount of the organic solvent at azeotropic temperature or higher for 30 minutes or more within 3 hours or less. When the amount removed by distillation is small or the reflux time is shorter than 30 minutes, the dehydration becomes insufficient and the remaining water induces side-reactions in the reaction, so that there is a concern that purity may decrease.

After the dehydration, a reaction solvent suitable for the reaction is added. The reaction solvent is preferably an organic solvent and is not particularly limited as far as it is an aprotic solvent. Preferred are solvents subjected to a dehydration treatment. Particularly preferred are chloroform, dichloromethane, tetrahydrofuran, acetonitrile, and dimethyl sulfoxide and further preferred are dichloromethane and chloroform. The amount of the organic solvent is 1 to 50 times by weight, preferably 2 to 30 times by weight, and further preferably 3 to 20 times by weight the amount of the mixture. The reason why the solvent having a low water content is used is to suppress the aforementioned side-reactions.

The amount of the phthalimide to be used for the phthalimide formation is 1 to 10 molar equivalents, preferably 1.01 to 5 molar equivalents, and further preferably 1.02 to 3 molar equivalents to the mixture of the compounds represented by the formulae (5) and (6).

The azo-based reagent to be used for the phthalimide formation includes 1,1'-azobis(N,N-dimethylformamide), 1,1'-(azodicarbonyl)dipiperidine, dibenzyl azodicarboxylate, diethyl azodicarboxylate, diisopropyl azodicarboxylate, dimethyl azodicarboxylate, 1,1'-azobis(N,N-diisopropylformamide), 1,6-dimethyl-1,5,7-hexahydro-1,4,6,7-tetrazocine-2,5-dione, and the like. Preferred are diethyl azodicarboxylate and diisopropyl azodicarboxylate and further preferred is diisopropyl azodicarboxylate. The amount of the azo-based reagent is 1 to 10 molar equivalents, preferably 1.01 to 5 molar equivalents, and further preferably 1.02 to 3 molar equivalents to the mixture of the compounds represented by the formulae (5) and (6).

The phosphine-based reagent to be used for the phthalimide formation includes dicyclohexylphenylphosphine, diethxylphenylphosphine, 4-(dimethylamino)phenylphosphine, diphenyl-2-pyridylphosphine, isopropyldiphenylphosphine, triisobutylphosphine, tri-n-butylphosphine, tri-t-butylphosphine, tricyclohexylphosphine, tri-n-hexylphosphine, tri-n-octylphosphine, and triphenylphosphine. The amount of the phosphine-based reagent is 1 to 10 molar equivalents, preferably 1.01 to 5 molar equivalents, and further preferably 1.02 to 3 molar equivalents to the mixture of the compounds represented by the formulae (5) and (6).

Phthalimide and the phosphine-based reagent are charged, finally, the azo-based reagent is gradually charged, and then the reaction is carried out. The reaction temperature is not particularly limited but is preferably room temperature. Moreover, the reaction time is preferably 5 minutes or more. When the time is less than 5 minutes, there is a concern that the conversion may decrease.

The reaction solution after the reaction contains the unreacted compound represented by the formula (6). A method for removing it is not particularly limited but it is preferred to separate the unreacted compound represented by the formula (6) by a purification means such as column chromatography, distillation, extraction, recrystallization, or supercritical extraction and purification by recrystallization is further preferred.

In the case of the purification by recrystallization, as good solvents, toluene, ethyl acetate, methanol, ethanol, acetonitile, and the like may be mentioned. Preferred are toluene, ethyl acetate, and ethanol and further preferred is ethyl acetate. One of these solvents can be used singly or two or more thereof can be used in combination. Moreover, as poor solvents, hexane, diethyl ether, methyl t-butyl ether, and the like may be mentioned and preferred is hexane. The amount of the good solvent is 1 to 50 times by weight, preferably 2.5 to 35 times by weight, and further preferably 5 to 20 times by weight the amount of the mixture. Moreover, the amount of the poor solvent is 0.5 to 30 times by weight, preferably 1 to 20 times by weight, and further preferably 2 to 10 times by weight.

The temperature for the recrystallization is −20 to 30° C., preferably −10 to 20° C. When the temperature exceeds 30° C., there is a concern that the crystals may be dissolved to decrease the yield. Moreover, the time for the recrystallization is preferably 15 minutes or more. When the time is less than 15 minutes, there is a concern that the removal of impurities may be insufficient. Purification efficiency is increased by repeating recrystallization and thus the number of times is not particularly limited but is preferably 1 to 5 times, further preferably 2 to 4 times. The crystals of the compound (17) obtained are dried under reduced pressure.

The step (E1-2) is a deprotection step of the compound (17) obtained in the step (E1-1). A method for deprotection is not particularly limited as far as it is a common deprotection method of phthalimides as described in PROTECTIVE GROUPS IN ORGANIC SYNTHESIS (THEODORA W. GREENE et al) and the like but it is preferred to use a deprotection reagent having an amino group.

A solvent to be used in the deprotection step includes dichloromethane, chloroform, methanol, ethanol, and the like and preferred are chloroform and ethanol. The amount of the solvent is 1 to 50 times by weight, preferably 2 to 30 times by weight, and further preferably 3 to 20 times by weight the amount of the compound represented by the formula (17).

The deprotection reagent to be used in the step (E1-2) is not particularly limited as far as it is an amine low-molecular-weight compound having a primary amino group. Specifically, hydrazine, ethylenediamine, trimethylenediamine, diethylenetriamine, and the like may be mentioned and preferred are hydrazine and ethylenediamine. The amount of the deprotection reagent is 1 to 30 molar equivalents, preferably 2 to 20 molar equivalents, and further preferably 3 to 10 molar equivalents to the compound represented by the formula (17).

The reaction temperature is not particularly limited but is preferably 10 to 80° C., further preferably 20 to 60° C. Moreover, the reaction time is 1 hour or more. When the time is shorter than 1 hour, there is a concern that the conversion may be low.

A purification method after completion of the reaction is not particularly limited but it is preferred to separate the compounds such as the deprotection reagent by a purification means such as column chromatography, distillation, extraction, recrystallization, or supercritical extraction and purification by extraction is further preferred.

In the case of the purification by extraction, an organic solvent includes toluene, dichloromethane, chloroform, methanol, and the like and preferred is dichloromethane. One of these solvents can be used singly or two or more thereof can be used in combination. The amount of the organic solvent is 1 to 20 times by weight, preferably 2 to 10 times by weight the amount of the compound represented by the formula (17). Moreover, an aqueous solution to be used is a 1 to 25% by weight aqueous solution of an alkali metal inorganic salt and the alkali metal inorganic salt is preferably an alkali metal halogen salt, more preferably sodium chloride. The amount of the aqueous solution is 1 to 20 times by weight, preferably 2 to 10 times by weight the amount of the compound represented by the formula (17).

The time for mixing and layer separation in the extraction step is not particularly limited but is preferably 1 minute to 6 hours, more preferably 10 minutes to 3 hours. Moreover, the extraction temperature is 10 to 80° C., preferably 20 to 60° C. Purification efficiency is improved by repeating the extraction. The number of times is not particularly limited but is preferably 1 to 4 times, further preferably 2 to 3 times. After the extraction, preferably, dehydration with a dehydration agent is performed. After filtration of the dehydration agent, the solvent is removed by distillation and thus the compound represented by the formula (16) can be obtained.

The step (E2) comprises two steps of the following (E2-1) and (E2-2).

The step (E2-1) is a step of converting both structural isomers into activated carbonates or sulfonates.

The step (E2-2) is a purification step of separating the structural isomers utilizing slight difference in a physical property between the functionalized structural isomers.

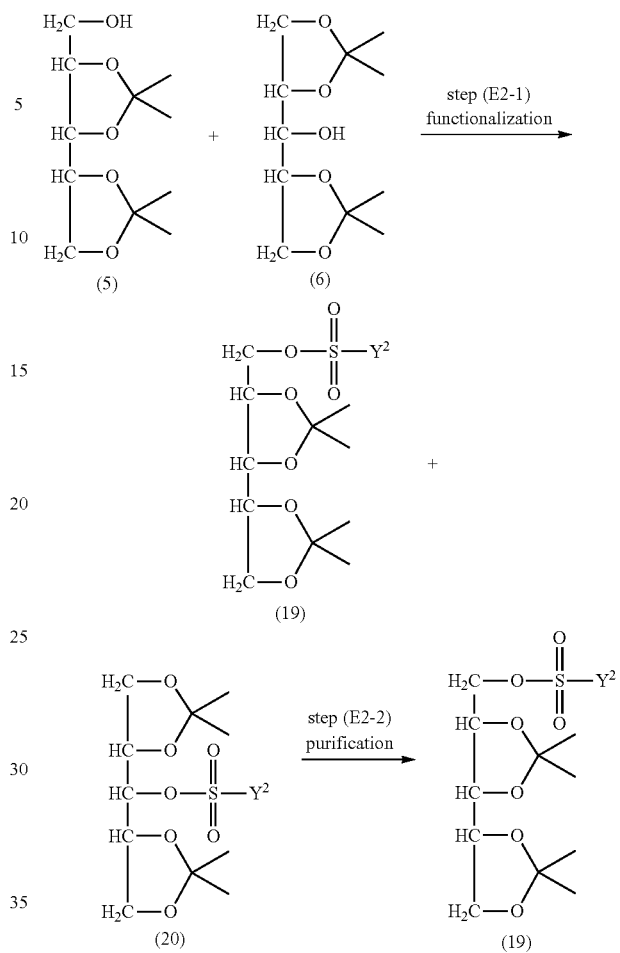

In the above process drawing, the compound (19) corresponds to the compound represented by the formula (12) in the above process drawing IV.

The step (E2-1) is a step of introducing an activated carbonate group and an activated sulfonate group by reacting the mixture of the compounds represented by the formulae (5) and (6) with either of the compounds represented by the following formulae (b1) and (e1) (compound (b1), compound (e1)), respectively. For example, in the activated sulfonate group, the compounds represented by the formulae (19) and (20) are obtained. In the cases where any of the activated carbonate group and the activated sulfonate group is introduced, they can be manufactured by about the same manufacturing method. Therefore, the following will describe the introduction of the activated sulfonate group.

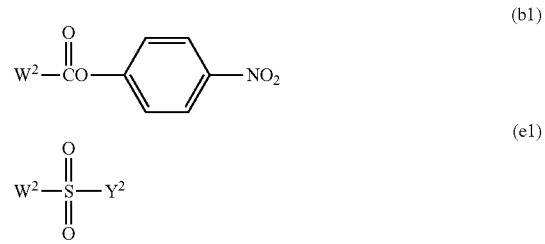

wherein $W^2$ and $Y^2$ have the same meanings as mentioned above.

The reaction solvent to be used in the step (E2-1) includes aprotic solvents such as toluene, acetonitrile, ethyl acetate, tetrahydrofuran, chloroform, and dichloromethane or no solvent, and preferred are toluene and chloroform. The amount of the solvent is 1 to 50 times by weight, preferably 2 to 30 times by weight, and further preferably 3 to 20 times by weight the amount of the mixture of the compounds represented by the formulae (5) and (6).

$W^2$ in the compound represented by the above general formula (e1) to be used in the step (E2-1) is a halogen atom selected from Cl, Br, and I and is preferably Cl. The amount of the compound represented by (e1) is not particularly limited but is 1 to 10 molar equivalents, preferably 1.01 to 5 molar equivalents, and further preferably 1.02 to 3 molar equivalents to the mixture of the compounds represented by the formulae (5) and (6).

The base to be used in the reaction includes organic bases such as triethylamine, pyridine, and 4-dimethylaminopyridine or inorganic bases such as sodium carbonate, sodium hydroxide, sodium hydrogen carbonate, sodium acetate, potassium carbonate, and potassium hydroxide and preferred is triethylamine. The amount of the base is not particularly limited but is 1 to 15 molar equivalents, preferably 1.1 to 10 molar equivalents, and further preferably 1.2 to 5 molar equivalents to the mixture.

The reaction temperature is not particularly limited but is preferably 0 to 80° C., further preferably 20 to 60° C. Moreover, the reaction time is 1 hour or more. When the time is shorter than 1 hour, there is a concern that the conversion may be low.

The step (E2-2) is a step of separation and purification of the mixture represented by the formulae (19) and (20) formed in the step (E2-1).

A purification method is not particularly limited but it is preferred to separate the compound represented by the formula (20) by a purification means such as column chromatography, distillation, extraction, recrystallization, or supercritical extraction and purification by recrystallization is further preferred.

In the case of the purification by recrystallization, as good solvents, toluene, ethyl acetate, methanol, ethanol, acetonitile, and the like may be mentioned. Preferred are toluene, ethyl acetate, and ethanol and further preferred is ethyl acetate. One of these solvents can be used singly or two or more thereof can be used in combination. Moreover, as poor solvents, hexane, diethyl ether, methyl t-butyl ether, and the like may be mentioned and preferred is hexane. The amount of the good solvent is 1 to 50 times by weight, preferably 2.5 to 35 times by weight, and further preferably 5 to 20 times by weight the amount of the mixture. Moreover, the amount of the poor solvent is 0.5 to 30 times by weight, preferably 1 to 20 times by weight, and further preferably 2 to 10 times by weight.

The temperature for the recrystallization is −20 to 30° C., preferably −10 to 20° C. When the temperature exceeds 30° C., there is a concern that the crystals may be dissolved to decrease the yield. Moreover, the time for the recrystallization is preferably 15 minutes or more. When the time is less than 15 minutes, there is a concern that the removal of impurities may be insufficient. Purification efficiency is increased by repeating recrystallization and thus the number of times is not particularly limited but is preferably 1 to 5 times, further preferably 2 to 4 times. The crystals of the compound (15) obtained are dried under reduced pressure.

The step (F) is a step of bonding the polyhydric alcohol derivative (12) functionalized in the step (E) to a polyoxyethylene derivative (21) by reaction as shown in the following process drawing (process drawing V).

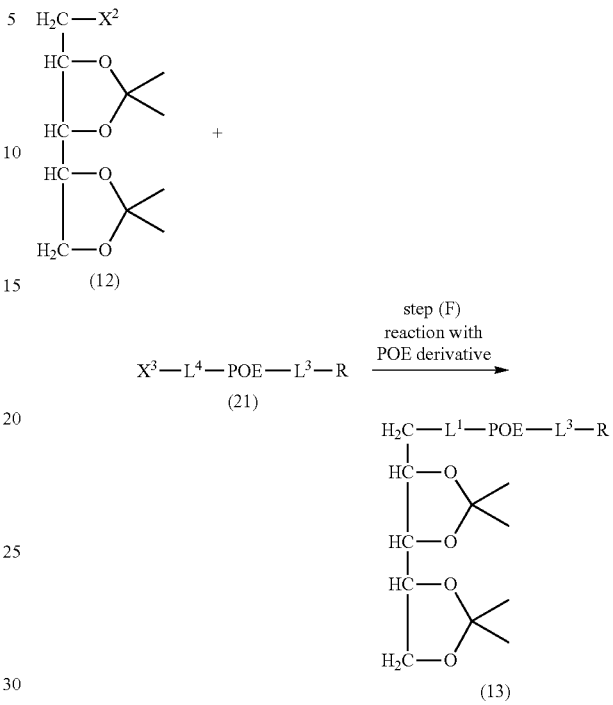

wherein POE, $L^1$, $L^3$, and $X^2$ have the same meanings as mentioned above; R represents a functional group protected with a protective group or a hydroxyl group which may be protected; $L^4$ is a linker; and $X^3$ is a functional group capable of reacting with $X^2$.

Specific examples of the linker $L^4$ are the same as those mentioned as specific examples of the linkers $L^1$ to $L^3$.

The polyoxyethylene derivative represented by the above formula (21) to be used in the step (F) has a functional group $X^3$ capable of reacting with $X^2$ of the compound represented by the formula (12). In the case where $X^2$ is an amino group, $X^3$ is not particularly limited as far as it is a functional group capable of reacting with the amino group and examples thereof are an active ester group, an active carbonate group, an aldehyde group, a substituted sulfonate group, a carboxyl group, and the like and preferred are an active ester group and an active carbonate group. In the case where $X^2$ is an active carbonate group or a sulfonate group, $X^3$ is not particularly limited as far as it is a functional group capable of reacting with the active carbonate group or sulfonate group and preferred are an amino group and an alkoxide group.

R represents a functional group protected with a protective group or a hydroxyl group which may be protected. The protected functional group includes an amino group, a carboxyl group, an aldehyde group, and a thiol group. A specific protective group for the amino group includes a t-butyl carbamate group, a benzyl group, a trityl group, and the like but preferred is a t-butyl carbamate group. A specific protective group for the carboxyl group includes a t-butyl group, a benzyl group, and the like but preferred is a benzyl group. A specific protective group for the aldehyde group includes an acetal group having 3 to 9 carbon atoms and the like but preferred is a diethyl acetal group. A specific protective group for the thiol group includes a t-butyl group, a benzyl group, a trityl group, a t-butyldimethylsilyl group, a t-butyldiphenylsilyl group, and the like but preferred are a t-butyl group and a benzyl group and further preferred is a t-butyl group.

Moreover, a specific protective group for the hydroxyl group includes a t-butyl group, a benzyl group, a trityl group, a t-butyldimethylsilylgroup, a t-butyldiphenylsilyl group, and the like but preferred are a t-butyl group and a benzyl group and further preferred is a benzyl group.

The amount of the compound represented by the formula (12) to be used in the step (F) is not particularly limited but is 1 to 20 molar equivalents, preferably 1.5 to 15 molar equivalents, and further preferably 2 to 10 molar equivalents to the polyoxyethylene derivative represented by the formula (21).

The reaction solvent to be used in the step (F) includes aprotic solvents such as toluene, acetonitrile, ethyl acetate, tetrahydrofuran, chloroform, and dichloromethane and preferred are toluene and chloroform. The amount of the solvent is 1 to 50 times by weight, preferably 2 to 25 times by weight, and further preferably 3 to 10 times by weight the amount of the compound represented by the formula (21).

The reaction temperature is not particularly limited but is preferably 0 to 100° C., further preferably 20 to 80° C. Moreover, the reaction time is 1 hour or more. When the time is shorter than 1 hour, there is a concern that the conversion may be low.

A purification method is not particularly limited but a purification means such as column chromatography, distillation, extraction, recrystallization, or supercritical extraction may be mentioned and purification by recrystallization is further preferred.

In the case of the purification by recrystallization, as good solvents, toluene, ethyl acetate, methanol, ethanol, acetonitrile, and the like may be mentioned. Preferred are toluene, ethyl acetate, and ethanol and further preferred is ethyl acetate. One of these solvents can be used singly or two or more thereof can be used in combination. Moreover, as poor solvents, hexane, diethyl ether, methyl t-butyl ether, and the like may be mentioned and preferred is hexane. The amount of the good solvent is 1 to 50 times by weight, preferably 2.5 to 35 times by weight, and further preferably 5 to 20 times by weight the amount of the mixture. Moreover, the amount of the poor solvent is 0.5 to 30 times by weight, preferably 1 to 20 times by weight, and further preferably 2 to 10 times by weight.

The temperature for the recrystallization is −20 to 30° C., preferably −10 to 20° C. When the temperature exceeds 30° C., there is a concern that the crystals may be dissolved to decrease the yield. Moreover, the time for the recrystallization is preferably 15 minutes or more. When the time is less than 15 minutes, there is a concern that the removal of impurities may be insufficient. Purification efficiency is increased by repeating recrystallization and thus the number of times is not particularly limited but is preferably 1 to 5 times, further preferably 2 to 4 times. The crystals of the compound (13) obtained are dried under reduced pressure.

The step (G) is a step of producing a functional group or a hydroxyl group by deprotection of the protective group R of the polyoxyethylene derivative represented by the formula (13) obtained in the step of (F). In the case where the hydroxyl group is produced, subsequently, a functional group is introduced by the same manufacturing method as the step (C) of the aforementioned process drawing II. Depending on the kind of the protective group of R at the polyoxyethylene terminal end, it is possible to perform deacetalization of the next step simultaneously with the deprotection in some cases.

As a method for deprotection of these protective groups, the deprotection can be performed using a common deprotection method as described in PROTECTIVE GROUPS IN ORGANIC SYNTHESIS (THEODORA W. GREENE et al) and the like.

After the deprotection, the product may be purified by a purification means such as extraction, recrystallization, adsorption treatment, reprecipitation, column chromatography, or supercritical extraction. Preferably, the compound represented by the formula (13) can be obtained by conducting recrystallization and drying the resulting crystals under reduced pressure.

The step (H) is a deprotection step of cleaving the cyclic acetal structure of the polyoxyethylene derivative represented by the formula (14) obtained in the step (G). Depending on the kind of the functional group at the polyoxyethylene terminal end, functionalization can be further performed after the step (H).

The step (H) is the same step as the step (D). By conducting the step (D), the compound represented by the formula (15) that is an objective compound can be obtained.

According to the invention, a polyoxyethylene derivative (1) having plural hydroxyl groups at a terminal end thereof can be industrially manufactured in high purity and in an efficient manner.

Moreover, the polyoxyethylene derivative (1) obtained by the invention has an advantage that half-lives in blood and antigenicity can be improved as compared with conventional polyoxyethylene derivatives and thus is useful for modifying bio-related substances.

EXAMPLES

The following will describe the invention more specifically based on Examples. In this regard, $^1$H-NMR and GPC were employed for analyzing and identifying the compounds in Examples.

<Method for $^1$H-NMR Analysis>

At $^1$H-NMR analysis, JNM-ECP400 manufactured by Nippon Denshi Datum K.K. was used. The integral values in NMR data are theoretical values.

<Method for GPC Analysis>

GPC analysis was carried out under the following conditions.

Apparatus: Shimadzu LC-10Avp
Column: PL gel MIXED-D×2 (Polymer Laboratory)
Developing solvent: dimethylformamide
Flow rate: 0.7 ml/min
Column temperature: 65° C.
Detector: RI
Sample amount: 1 mg/g, 100 μl
The molecular weight is a peak top molecular weight Mp.

Example 1

Synthesis of Polyoxyethylene Derivative (1)

(case where $L^1$=—O—, $L^3$=—$CH_2CH_2$—NHCO—$CH_2CH_2$—, X=maleimido group, Z=ethylene glycol residual group, a=1, b=1, c=1, d=0, e=1, and molecular weight=about 20000)

Example 1-1

Compound (5) (6): Synthesis of Diisopropylidenexylitol

In a 5 L round-bottom flask fitted with a thermometer, a nitrogen-introducing tube, and a stirrer were placed 1000 g of xylitol, 1916 g of 2,2-dimethoxypropane, and 37.5 mg of p-toluenesulfonic acid monohydrate and, with introduction of nitrogen thereinto, the reaction was carried out at 65° C. The solvent of the reaction solution was removed by distillation and purification by distillation (b.p. 108° C./0.15 mmHg) was performed to obtain an isomer mixture of 1,2,3,4-diisopropylidenexylitol (formula (5)) and 1,2,4,5-diisopropylidenexylitol (formula (6)). ¹H-NMR (CDCl₃, internal standard TMS) δ (ppm): 1.37-1.44 (12H, m, —C(CH₃)₂), 3.59-3.65 (1H, m, —CH—O—), 3.81-3.90 (2H, m, —CH₂—O—), 3.98-4.01 (1H, m, —CH—O—), 4.04-4.10 (2H, m, —CH₂—O—), 4.11-4.23 (1H, m, —CH—O—) 1H, m, —CH—O—)

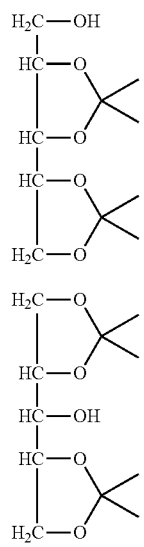

(5)

(6)

Example 1-2

Compound (7): Synthesis of 1,2,3,4-diisopropylidene-5-(t-butyldiphenylsilyl)xylitol In a 2 L round-bottom flask fitted with a thermometer, a nitrogen-introducing tube, and a stirrer were placed 250 g of diisopropylidenexylitol (isomer mixture) purified in 1-1, 1000 g of dichloromethane, 26 g of 4-dimethylaminopyridine, and 109 g of triethylamine, and the whole were dissolved with introduction of nitrogen thereinto. After cooling to 10° C. or lower, 297 g of t-butylchlorodiphenylsilane was added dropwise thereto. After the dropwise addition, temperature was returned to room temperature and, after the reaction for 2 hours, a saturated aqueous sodium hydrogen carbonate solution was added and washing was performed. After dehydration over magnesium sulfate, the solvent was removed by distillation and 1,2,4,5-diisopropylidenexylitol was removed at 135° C. under reduced pressure (0.2 mmHg) to obtain 200 g of 1,2,3,4-diisopropylidene-5-(t-butyldiphenylsilyl)xylitol (formula (7)). ¹H-NMR (CDCl₃, internal standard TMS) δ (ppm): 1.06 (9H, m, —Si—C—(CH₃)₃), 1.37, 1.42, 1.43 (12H, s, —O—C—CH₃), 3.72-3.82 (1H, m, —CH—O—, —CH₂—O—), 3.95 (1H, dd, —CH—O—), 3.99-4.06 (2H, m, —CH₂—O—), 4.11-4.15 (1H, m, —CH—O—), 7.36-7.54 (6H, m, Ph-Si(-Ph)-O—), 7.66-7.70 (4H, m, Ph-Si(-Ph)-O—)

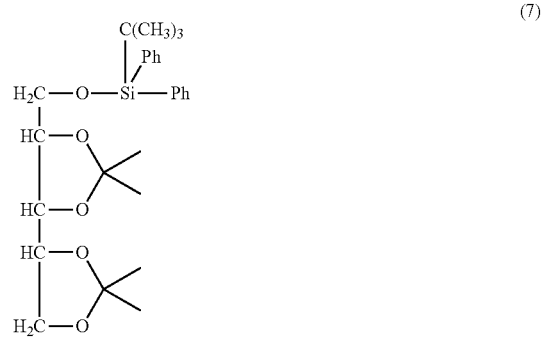 [SMILES: CC1(C)OCC(C2OC(C)(C)OC2CO[Si](c2ccccc2)(c2ccccc2)C(C)(C)C)O1]

(7)

Example 1-3

Compound (5): Synthesis of 1,2,3,4-diisopropylidenexylitol

In a 2 L round-bottom flask fitted with a thermometer, a nitrogen-introducing tube, and a stirrer were placed 500 g of 1,2,3,4-diisopropylidene-5-(t-butyldiphenylsilyl)xylitol and 440 g of dehydrated tetrahydrofuran, and they were homogenized at room temperature with introduction of nitrogen thereinto. After cooling to 20° C. or lower, 1270 ml of tetrabutylammonium fluoride (1 mol/L tetrahydrofuran solution) was added dropwise thereto. After the dropwise addition, temperature was returned to room temperature and, after the reaction for 2 hours, the solvent was removed by distillation under reduced pressure. The residue was dissolved with 2000 g of ethyl acetate and then the ethyl acetate layer was washed with purified water. After dehydration over magnesium sulfate, the solvent was removed by distillation and 250 g of 1,2,3,4-diisopropylidenexylitol (formula (5)) was obtain by column chromatography using chloroform and methanol as solvents and silica gel as a filler. ¹H-NMR (CDCl₃, internal standard TMS) δ (ppm): 1.39, 1.44 (12H, s, —CH₃), 3.62 (1H, dd, —CH—O—), 3.08-3.89 (2H, m, —CH₂—O—), 3.98-4.08 (1H, m, —CH—O—, 2H, m, —CH₂—O—), 4.18-4.23 (1H, m, —CH—O—)

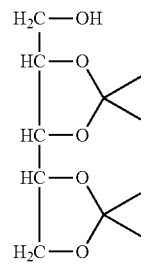

(5)

Example 1-4

Compound (p1): Synthesis of α-diisopropylidenexylitol polyoxyethylene (molecular weight: 20,000)

Into a 5 L autoclave were charged 100 g (0.43 mol) of 1,2,3,4-diisopropylidenexylitol (5), 200 g of dehydrated toluene, and 10.8 g of a 28% methanol solution of sodium methoxide. After the inside of the system was replaced by nitrogen, the temperature was elevated to 50° C. and toluene and methanol were removed by distillation. After 4205 g (95.6 mol) of ethylene oxide was added at a pressure of 1 MPa or lower at 100 to 150° C., the reaction was continued for another 1 hour and then a half of the content, 2150 g, was taken out. Subsequently, after 2150 g (48.9 mol) of ethylene oxide was added at a pressure of 1 MPa or lower at 100 to 150° C., the reaction was continued for another 1 hour. After unreacted ethylene oxide gas was removed under reduced pressure, the following compound (p1) was obtained.

$^1$H-NMR (CDCl$_3$, internal standard TMS) δ (ppm): 1.37-1.44 (12H, m, —C(C$\underline{H}_3$)$_2$), 3.40-3.90 (about 1880H, m, —C$\underline{H}_2$O(C$\underline{H}_2$C$\underline{H}_2$O)$_m$H)

Molecular weight (GPC/Mp): 20678 (m=about 470)

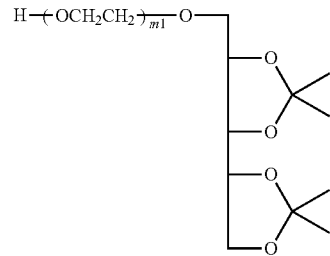

m1= about 470 (p1)

Example 1-5

Compound (p2): Synthesis of α-diisopropylidenexylitol ω-amine polyoxyethylene (molecular weight: 20,000)

Into a 1 L four-neck flask fitted with a thermometer, a nitrogen-introducing tube, a stirrer, a Dean-Stark tube, and a cooling tube were charged 200 g (10 mmol) of α-diisopropylidenexylitol polyoxyethylene (p1) and 600 g of toluene, and the whole was heated to 60° C. and dissolved with stirring and introduction of nitrogen. The temperature was elevated to 110° C. and about 300 g of a fraction was taken out as an azeotrope with toluene to perform dehydration. After cooling to 40° C., 1.0 kg of dehydrated acetonitrile was added and 2.2 g (15 mmol) of phthalimide and 3.9 g (15 mmol) of triphenylphosphine were added. Thereafter, 3.0 g (15 mmol) of diisopropyl azodicarboxylate was added, followed by the reaction at room temperature for 2 hours.

After the reaction, the solvent was removed by distillation and 400 g of methanol and 30 g (0.5 mol) of ethylenediamine were added, followed by the reaction at 60° C. for 4 hours. The whole was diluted with 1.0 kg of dichloromethane and extraction was performed twice with 500 g of a 25% aqueous sodium chloride solution. About 1.5 kg of a fraction was taken out at 40° C. under slightly reduced pressure, then cooling was performed to room temperature, 600 g of ethyl acetate was added thereto, and magnesium sulfate was added to perform dehydration. After magnesium sulfate was filtrated, 600 g of n-hexane was added to the filtrate to precipitate crystals. After the crystals were collected by filtration, they were dissolved in 800 g of ethyl acetate at 40° C. and, after cooling to room temperature, 600 g of n-hexane was added thereto to precipitate crystals. The crystals collected by filtration were washed with 1.0 kg of n-hexane. The crystals were collected by filtration and dried under vacuum to obtain 184 g of the following compound (p2).

$^1$H-NMR (D$_2$O) δ (ppm): 1.37-1.44 (12H, m, —C(C$\underline{H}_3$)$_2$), 2.84-2.88 (2H, t, —C$\underline{H}_2$—NH$_2$), 3.40-3.90 (about 1880H, m, —C$\underline{H}_2$O(C$\underline{H}_2$C$\underline{H}_2$O)$_m$—C$\underline{H}_2$O—)

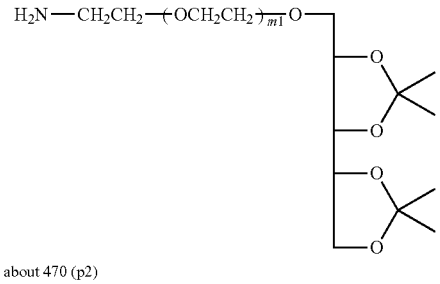

m1 = about 470 (p2)

Example 1-6

Compound (p3): Synthesis of α-xylitol ω-amine polyoxyethylene (molecular weight: 20,000)

Into a 3 L three-neck flask fitted with a thermometer and a stirrer were charged 100 g (5 mmol) of α-diisopropylidenexylitol ω-amine polyoxyethylene (p2) and 1.8 kg of ion-exchange water, and the whole was dissolved with stirring and introduction of nitrogen. With adding 85% phosphoric acid dropwise, the addition was performed so as to be pH 1.4 and the reaction was carried out at room temperature for 8 hours.

After the reaction, the mixture was neutralized with adding a 10N aqueous sodium hydroxide solution and, after the addition of 360 g of sodium chloride, was adjusted to pH 12.0 by further adding a 10N aqueous sodium hydroxide solution. Thereto was added 500 g of toluene, followed by extraction at 50° C. twice. The solvent was removed under reduced pressure, 500 g of ethyl acetate was added, and magnesium sulfate was added to perform dehydration. After magnesium sulfate was filtrated off, 400 g of n-hexane was added to the filtrate to precipitate crystals. The crystals collected by filtration were washed with 400 of n-hexane. The crystals were collected by filtration and dried under vacuum to obtain 90 g of the following compound (p3).

$^1$H-NMR (D$_2$O) δ (ppm): 2.84-2.88 (2H, t, —C$\underline{H}_2$—NH2), 3.40-3.90 (about 1880H, m, —C$\underline{H}_2$O(C$\underline{H}_2$C$\underline{H}_2$O)$_m$—C$\underline{H}_2$O—)

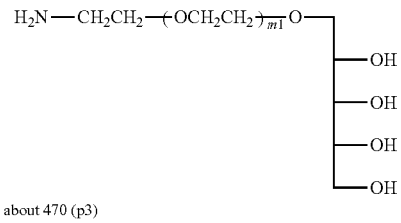

m1 = about 470 (p3)

Example 1-7

Compound (p4): Synthesis of α-xylitol ω-maleimide polyoxyethylene (molecular weight: 20,000)

Into a 100 mL four-neck flask fitted with a thermometer, a nitrogen-introducing tube, a stirrer, and a cooling tube were charged 10 g (0.5 mmol) of α-xylitol ω-amine polyoxyethylene (p3) and 50 g of toluene, and the whole was heated to 40° C. and dissolved. After light shielding, 160 mg (0.6 mmol) of N-succinimidylmaleimide propionate was added and the reaction was carried out at 40° C. for 4 hours.

After the reaction, filtration was performed and 30 g of ethyl acetate was added to dilute the filtrate, followed by addition of 40 g of n-hexane to precipitate crystals. After the crystals were collected by filtration, they were dissolved in 100 g of ethyl acetate at 40° C. and, after cooling to room temperature, 50 g of n-hexane was added thereto to precipitate crystals. The dissolution of the crystals and the crystallization step were further repeated once. The crystals collected by filtration were washed with 50 g of n-hexane. The crystals were collected by filtration and dried under vacuum to obtain 9 g of the following compound (p4).

$^1$H-NMR (CDCl$_3$, internal standard TMS) δ (ppm): 2.49-2.54 (2H, t, —NHCO<u>CH$_2$</u>CH$_2$—), 3.40-3.90 (about 1880H, m, —<u>CH$_2$</u>O(<u>CH$_2$CH$_2$</u>O)$_m$—<u>CH$_2$</u>, —<u>CH$_2$</u>NHCO—), 6.70 (2H, s, —<u>CH=CH</u>—)

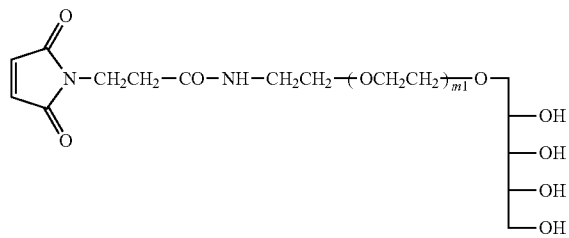

m1 = about 470 (p4)

Example 2

Synthesis of Polyoxyethylene Derivative (1)

(case where L$^1$=-OCO—NH—, X=p-nitrophenyl carbonate group, Z=glycerin residual group, a=1, b=2, c=1, d=0, e=0, and molecular weight=about 40000)

Example 2-1

Synthesis of Compound (17)

Into a 1 L four-neck flask fitted with a thermometer, a nitrogen-introducing tube, a stirrer, a Dean-Stark tube, and a cooling tube were charged 50 g (0.22 mol) of diisopropylidenexylitols (5) (6) and 100 g of toluene. With stirring and introduction of nitrogen, the temperature was elevated to 110° C. and about 80 g of a fraction was taken out as an azeotrope with toluene to perform dehydration. After cooling to 40° C., 500 g of dehydrated acetonitrile was added and 31.7 g (0.22 mol) of hydroxyphthalimide and 56.5 g (0.22 mol) of triphenylphosphine were added. Thereafter, 43.5 g (0.22 mol) of diisopropyl azodicarboxylate was slowly added and the reaction was carried out at room temperature for 2 hours.

After the reaction, the solvent was removed by distillation and, after 500 g of ethyl acetate, 300 g of ethanol, and 200 g of n-hexane were added thereto, the whole was cooled to 10° C. or lower to precipitate crystals. The crystals were collected by filtration and dried under vacuum to obtain 50 g of the following compound (17).

$^1$H-NMR (CDCl$_3$, internal standard TMS) δ (ppm): 1.34-1.44 (12H, m, —C(<u>CH$_3$</u>)$_2$), 3.80-3.90 (2H, m, N—<u>CH$_2$</u>—CH), 3.93-4.02 (2H, m, —<u>CH$_2$</u>—O—), 4.07-4.12 (1H, m, —<u>CH</u>—O—), 4.23-4.32 (2H, m, —<u>CH</u>—O—), 7.71-7.89 (4H, m, <u>Ph</u>)

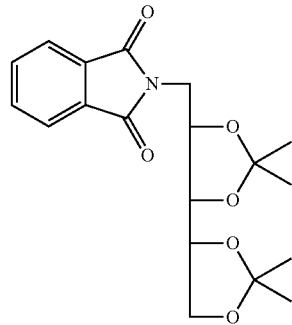

Example 2-2

Synthesis of Compound (18)

Into a 1 L four-neck flask fitted with a thermometer, a nitrogen-introducing tube, a stirrer, and a cooling tube were charged 25 g (69 mmol) of the compound (15), 125 g of chloroform, and 20.8 g (0.345 mol) of ethylenediamine, followed by the reaction at 60° C. for 4 hours. Thereto was added 100 g of a 25% aqueous sodium chloride solution, extraction was performed twice, and magnesium sulfate was added to perform dehydration. After magnesium sulfate was filtrated off, the solvent was removed by distillation under reduced pressure and the residue was dried under vacuum to obtain 12.5 g of the following compound (18) as a viscous liquid.

$^1$H-NMR (CDCl$_3$, internal standard TMS) δ (ppm): 1.36-1.44 (12H, m, —C(<u>CH$_3$</u>)$_2$), 2.78-2.96 (2H, m, —<u>CH$_2$</u>—NH$_2$), 3.81-3.86 (2H, m, —<u>CH$_2$</u>—O—), 3.95-3.99 (1H, m, —<u>CH</u>—O—), 4.03-4.06 (1H, m, —<u>CH</u>—O—), 4.15-4.19 (1H, m, —<u>CH</u>—O—)

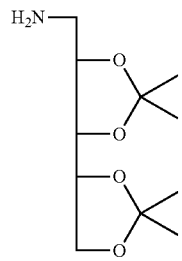

Example 2-3

Synthesis of Polyoxyethylene Derivative (p6)
(Molecular Weight: 40,000)

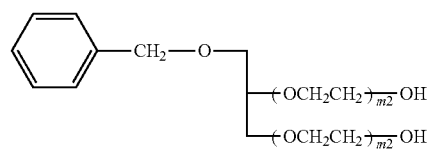

m2 = about 480 (p5)

Into a 1 L four-neck flask fitted with a thermometer, a nitrogen-introducing tube, a stirrer, a Dean-Stark tube, and a cooling tube were added 100 g (2.5 mmol) of the above compound (p5) that was a double-branched PEG having a molecular weight of 40,000 synthesized in accordance with Example 16 of JP-A-2004-197077 and 500 g of toluene. With stirring and introduction of nitrogen, the whole was heated to 60° C. and dissolved. The temperature was elevated to 110° C. and about 100 g of a fraction was taken out as an azeotrope with toluene to perform dehydration. After cooling to 60° C., 1.5 g (15.0 mmol) of triethylamine and 2.5 g (12.5 mmol) of p-nitrophenyl chloroformate were added, followed by the reaction at 60° C. for 6 hours.

Thereto was added 300 g of toluene for dilution and, after filtration, 300 g of n-hexane was added to precipitate crystals. After the crystals were collected by filtration, they were dissolved in 700 g of ethyl acetate at 40° C. and, after cooling to room temperature, 300 g of n-hexane was added to precipitate crystals. The dissolution of crystals and the crystallization step were further repeated twice. The crystals collected by filtration were washed with 500 g of n-hexane. The crystals were collected by filtration and dried under vacuum to obtain 94 g of the following compound (p6).

$^1$H-NMR (CDCl$_3$, internal standard TMS) δ (ppm): 3.40-3.80 (about 3840H, m, —CH$_2$(OCH$_2$CH$_2$)$_m$OCH$_2$CH$_2$—O—CO—, —CH(OCH$_2$CH$_2$)$_m$OCH$_2$CH$_2$—O—CO—, —CH$_2$—O—CH$_2$-Ph), 4.44 (4H, t, —OCH$_2$CH$_2$—O—CO—O—), 4.54 (2H, s, —O—CH$_2$-Ph), 7.39 (4H, d, -Ph-NO$_2$), 8.28 (4H, d, -Ph-NO$_2$) Molecular weight (GPC/Mp): 42273 (m=about 480)

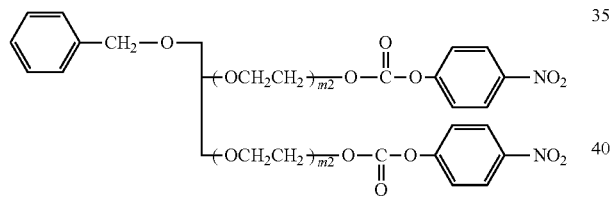

m2 = about 480 (p6)

Example 2-4

Synthesis of Polyoxyethylene Derivative (p7) (Molecular Weight: 40,000)

Into a 500 mL four-neck flask fitted with a thermometer, a nitrogen-introducing tube, a stirrer, and a cooling tube were charged 50 g (1.25 mmol) of the compound (p11) and 250 g of toluene. With stirring and introduction of nitrogen, the whole was heated to 40° C. and dissolved. The compound (18) was added in an amount of 1.2 g (5.0 mmol) and the reaction was carried out at 40° C. for 4 hours.

After the reaction, the mixture was diluted with 250 g of ethyl acetate and, after cooling to room temperature, 200 g of n-hexane was added to precipitate crystals. After the crystals were collected by filtration, they were dissolved in 500 g of ethyl acetate at 40° C. and, after cooling to room temperature, 200 g of n-hexane was added to precipitate crystals. The dissolution of crystals and the crystallization step were further repeated twice. The crystals collected by filtration were washed with 200 g of n-hexane. The crystals were collected by filtration and dried under vacuum to obtain 44 g of the following compound (p7).

$^1$H-NMR (CDCl$_3$, internal standard TMS) δ (ppm): 1.36-1.44 (24H, m, —C(CH$_3$)$_2$), 3.40-3.80 (about 3840H, m, —CH$_2$(OCH$_2$CH$_2$)$_m$OCH$_2$CH$_2$—O—CO—, —CH(OCH$_2$CH$_2$)$_m$OCH$_2$CH$_2$—O—CO—, —CH$_2$—O—CH$_2$-Ph), 4.02-4.09 (4H, m, —CH—O—), 4.15-4.25 (6H, m, —NH—CH$_2$—CH—O—, —OCH$_2$CH$_2$—O—CO—NH—), 4.54 (2H, s, —O—CH$_2$-Ph)

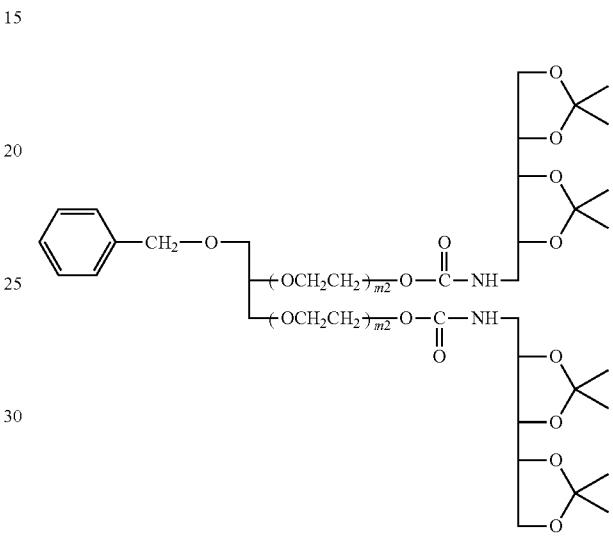

m2 = about 480 (p7)

Example 2-5

Synthesis of Polyoxyethylene Derivative (p8) (Molecular Weight: 40,000)

Into a 500 mL three-neck flask fitted with a thermometer and a stirrer were charged 40 g (1.0 mmol) of the compound (p7) and 20 g of 5% palladium carbon (50% hydrous product). After replacement by nitrogen, 400 mL of methanol and 67 mL of cyclohexene were added thereto and the whole was heated and gently refluxed at 52 to 55° C. to perform the reaction for 3 hours. After cooling to room temperature, palladium carbon was removed by filtration and the filtrate was concentrated. Then, 350 g of toluene and 250 g of n-hexane were added to the concentrate to precipitate crystals. The crystals collected by filtration were washed with 200 g of n-hexane. The crystals were collected by filtration and dried under vacuum to obtain 36 g of the following compound (p8).

$^1$H-NMR (CDCl$_3$, internal standard TMS) δ (ppm): 1.36-1.44 (24H, m, —C(CH$_3$)$_2$), 3.40-3.80 (about 3840H, m, —CH$_2$(OCH$_2$CH$_2$)$_m$OCH$_2$CH$_2$—O—CO—, —CH(OCH$_2$CH$_2$)$_m$OCH$_2$CH$_2$—O—CO—, —CH$_2$—OH), 4.02-4.09 (4H, m, —CH—O—), 4.15-4.25 (6H, m, —NH—CH$_2$—CH—O—, —OCH$_2$CH$_2$—O—CO—NH—)

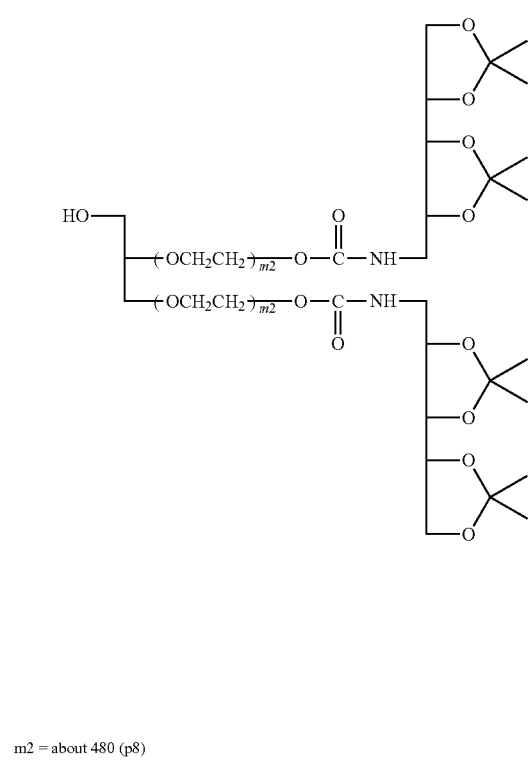

m2 = about 480 (p8)

Example 2-6

Synthesis of Polyoxyethylene Derivative (p9)
(Molecular Weight: 40,000)

Into a 300 mL four-neck flask fitted with a thermometer, a nitrogen-introducing tube, a stirrer, and a cooling tube were added 30 g (0.75 mmol) of the compound (p8) and 150 g of toluene. With stirring and introduction of nitrogen, the whole was heated to 60° C. and dissolved. Then, 228 mg (2.25 mmol) of triethylamine and 378 mg (1.88 mmol) of p-nitrophenyl chloroformate were added, followed by the reaction at 60° C. for 4 hours.

Thereto was added 150 g of toluene for dilution and, after filtration, 120 g of n-hexane was added to precipitate crystals. After the crystals were collected by filtration, they were dissolved in 210 g of ethyl acetate at 40° C. and, after cooling to room temperature, 90 g of n-hexane was added to precipitate crystals. The dissolution of crystals and the crystallization step were further repeated twice. The crystals collected by filtration were washed with 90 g of n-hexane. The crystals were collected by filtration and dried under vacuum to obtain 26 g of the following compound (p9).

$^1$H-NMR (CDCl$_2$, internal standard TMS) δ (ppm): 1.36-1.44 (24H, m, —C(C$\underline{H}_3$)$_2$), 3.40-3.80 (about 3840H, m, —C$\underline{H}_2$(OC$\underline{H}_2$C$\underline{H}_2$)$_m$OC$\underline{H}_2$C$\underline{H}_2$—O—CO—, —C$\underline{H}$(O C$\underline{H}_2$C$\underline{H}_2$)$_m$OC$\underline{H}_2$C$\underline{H}_2$—O—CO—), 4.02-4.09 (4H, m, —C$\underline{H}$—O—), 4.15-4.25 (6H, m, —NH—CH$_2$—C$\underline{H}$—O—, —OC$\underline{H}_2$C$\underline{H}_2$—O—CO—NH—), 4.32-4.50 (2H, m, —C$\underline{H}_2$—O—OC—O-Ph-NO$_2$), 7.39 (2H, d, -$\underline{Ph}$-NO$_2$), 8.28 (2H, d, -$\underline{Ph}$-NO$_2$)

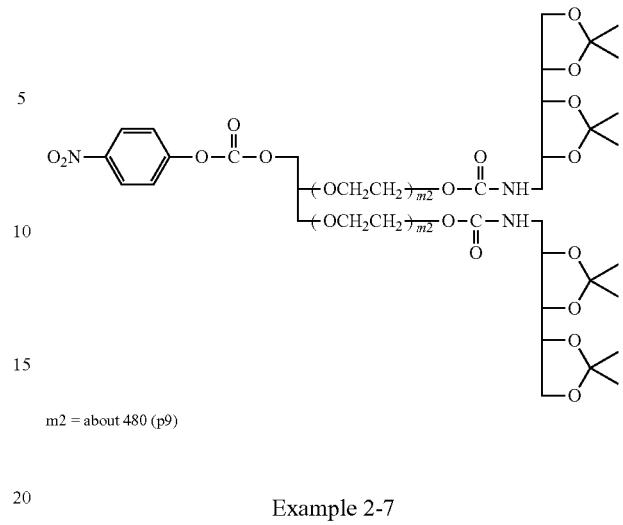

m2 = about 480 (p9)

Example 2-7

Synthesis of Polyoxyethylene Derivative (p10)
(Molecular Weight: 40,000)

Into a 500 mL three-neck flask fitted with a thermometer and a stirrer were charged 25 g (0.63 mmol) of the compound (p9) and 450 g of ion-exchange water, and the whole was dissolved with stirring and introduction of nitrogen. With adding 85% phosphoric acid dropwise, the addition was performed so as to be pH 1.0 and the reaction was carried out at room temperature for 3 hours.

After the reaction, 250 g of chloroform was added, followed by extraction at room temperature twice. Magnesium sulfate was added to perform dehydration. After magnesium sulfate was filtrated off, the solvent was removed by distillation under reduced pressure. Then, 150 g of ethyl acetate and 100 g of n-hexane were added thereto to precipitate crystals. The crystals collected by filtration were washed with 100 g of n-hexane. The crystals were collected by filtration and dried under vacuum to obtain 20 g of the following compound (p10).

$^1$H-NMR (CDCl$_3$, internal standard TMS) δ (ppm): 3.40-3.80 (about 3840H, m, —C$\underline{H}_2$(OC$\underline{H}_2$C$\underline{H}_2$)$_m$O C$\underline{H}_2$C$\underline{H}_2$—O—CO—, —C$\underline{H}$(OC$\underline{H}_2$C$\underline{H}_2$)$_m$O C$\underline{H}_2$C$\underline{H}_2$—O—CO—), 4.02-4.09 (4H, m, —C$\underline{H}$—O—), 4.15-4.25 (6H, m, —NH—CH$_2$—C$\underline{H}$—O—, —OC$\underline{H}_2$ C$\underline{H}_2$—O—CO—NH—), 4.32-4.50 (2H, m, —C$\underline{H}_2$—O—CO—O-Ph-NO$_2$), 7.39 (2H, d, -$\underline{Ph}$-NO$_2$), 8.28 (2H, d, -$\underline{Ph}$-NO$_2$)

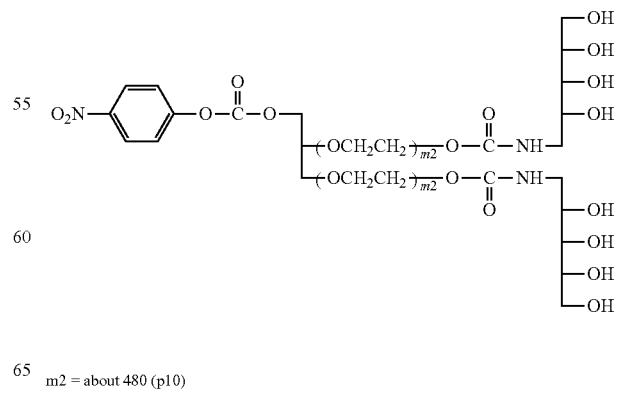

m2 = about 480 (p10)

What is claimed is:

1. A polyoxyethylene derivative represented by the formula (2):

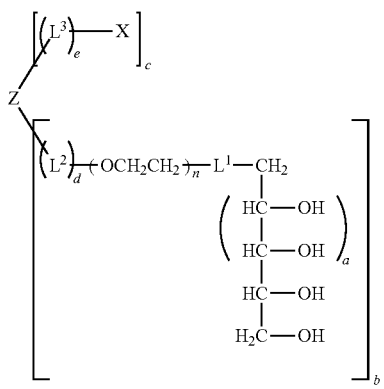

wherein a whole molecular weight of the polyoxyethylene derivative is 500 to 160,000; n is 5 to 3650; $L^1$, $L^2$, and $L^3$ each independently represent an alkylene group, a phenylene group, an ester bond, an amide bond, an ether bond, a urethane bond, a carbonate bond, a secondary amino group, or a combination thereof; X represents a functional group capable of reacting with a bio-related substance; Z represents a residual group of a compound having 2 to 5 active hydrogen atoms; a is 1 or 2; b and c are as follows: $1 \leq b \leq 4$, $1 \leq c \leq 4$, and $2 \leq b+c \leq 5$; and d and e are 0 or 1.

2. The polyoxyethylene derivative according to claim 1, which is a polyoxyethylene derivative represented by the following formula (3), wherein Z is an ethylene glycol residual group, b is 1, c is 1, d is 0, and e is 1 in the formula (2):

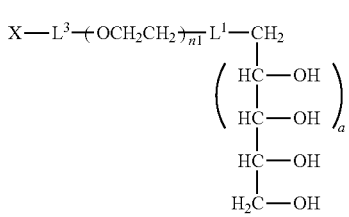

wherein $L^1$ and $L^3$ each independently represent an alkylene group, a phenylene group, an ester bond, an amide bond, an ether bond, a urethane bond, a carbonate bond, a secondary amino group, or a combination thereof; X represents a functional group capable of reacting with a bio-related substance; a is 1 or 2; and n1 is 11 to 3650.

3. The polyoxyethylene derivative according to claim 1, which is a polyoxyethylene derivative represented by the following formula (4), wherein Z is a glycerin residual group, b is 2, c is 1, and d is 0 in the formula (2):

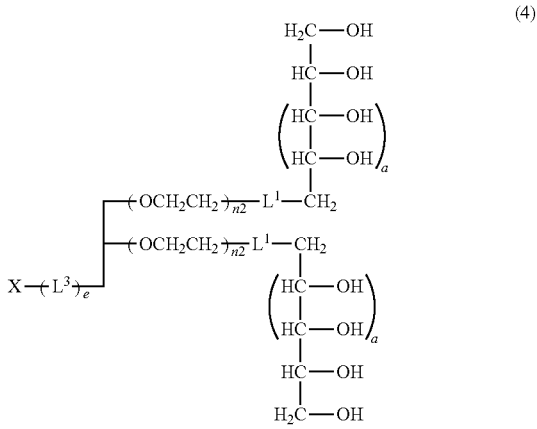

wherein $L^1$ and $L^3$ each independently represent an alkylene group, a phenylene group, an ester bond, an amide bond, an ether bond, a urethane bond, a carbonate bond, a secondary amino group, or a combination thereof; X represents a functional group capable of reacting with a bio-related substance; a is 1 or 2; e is 0 or 1; and n2 is 11 to 1825.

4. The polyoxyethylene derivative according to claim 1, wherein, in the formula (2), X is an active ester group, an active carbonate group, an aldehyde group, an isocyanate group, an isothiocyanate group, an epoxy group, a carboxyl group, a thiol group, a maleimido group, a substituted maleimido group, a hydrazido group, a dithiopyridine group, a substituted sulfonate group, a vinylsulfone group, an amino group, an oxyamino group, an iodoacetamido group, an alkylcarbonyl group, an alkenyl group, an alkynyl group, or an azido group.

5. The polyoxyethylene derivative according to claim 2, wherein, in the formula (3), X is an active ester group, an active carbonate group, an aldehyde group, an isocyanate group, an isothiocyanate group, an epoxy group, a carboxyl group, a thiol group, a maleimido group, a substituted maleimido group, a hydrazido group, a dithiopyridine group, a substituted sulfonate group, a vinylsulfone group, an amino group, an oxyamino group, an iodoacetamido group, an alkylcarbonyl group, an alkenyl group, an alkynyl group, or an azido group.

6. The polyoxyethylene derivative according to claim 3, wherein, in the formula (4), X is an active ester group, an active carbonate group, an aldehyde group, an isocyanate group, an isothiocyanate group, an epoxy group, a carboxyl group, a thiol group, a maleimido group, a substituted maleimido group, a hydrazido group, a dithiopyridine group, a substituted sulfonate group, a vinylsulfone group, an amino group, an oxyamino group, an iodoacetamido group, an alkylcarbonyl group, an alkenyl group, an alkynyl group, or an azido group.

* * * * *